(12) United States Patent
Ermann et al.

(10) Patent No.: US 8,329,735 B2
(45) Date of Patent: *Dec. 11, 2012

(54) TETRAZOLE COMPOUNDS WHICH SELECTIVELY MODULATE THE CB2 RECEPTOR

(75) Inventors: Monika Ermann, Wantage (GB); Doris Riether, Biberach an der Riss (DE); Renee M. Zindell, New Milford, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/037,422

(22) Filed: Mar. 1, 2011

(65) Prior Publication Data

US 2012/0071529 A1 Mar. 22, 2012

Related U.S. Application Data

(60) Provisional application No. 61/310,743, filed on Mar. 5, 2010.

(51) Int. Cl.
- A61K 31/44 (2006.01)
- A61K 31/421 (2006.01)
- C07D 249/14 (2006.01)
- A61P 25/00 (2006.01)

(52) U.S. Cl. ......... 514/363; 514/381; 548/139; 548/250
(58) Field of Classification Search .................. 514/363, 514/381; 548/139, 250
See application file for complete search history.

(56) References Cited

U.S. PATENT DOCUMENTS

| | | |
|---|---|---|
| 3,116,284 A | 12/1963 | Testa |
| 3,117,128 A | 1/1964 | Mooradian |
| 3,577,462 A | 5/1971 | Bruce et al. |
| 3,966,809 A | 6/1976 | Baker et al. |
| 4,257,954 A | 3/1981 | Schmidt et al. |
| 4,535,087 A | 8/1985 | Spatz |
| 4,672,065 A | 6/1987 | Spatz |
| 4,734,125 A | 3/1988 | Gehring et al. |
| 4,859,707 A | 8/1989 | Loftsson et al. |
| 5,256,658 A | 10/1993 | Hsi et al. |
| 5,428,037 A | 6/1995 | Pascal et al. |
| 5,475,130 A | 12/1995 | Sato et al. |
| 5,571,921 A | 11/1996 | Bender et al. |
| 5,583,147 A | 12/1996 | Ko et al. |
| 5,656,634 A | 8/1997 | Chang et al. |
| 5,847,153 A | 12/1998 | Warpehoski et al. |
| 5,958,940 A | 9/1999 | Rane et al. |
| 5,968,929 A | 10/1999 | Blythin et al. |
| 6,057,371 A | 5/2000 | Glennon |
| 6,176,442 B1 | 1/2001 | Eicher et al. |
| 6,221,866 B1 | 4/2001 | Brendel et al. |
| 6,355,653 B1 | 3/2002 | Trottmann et al. |
| 6,359,009 B1 | 3/2002 | Diehl et al. |
| 6,410,792 B1 | 6/2002 | Connell et al. |
| 6,414,011 B1 | 7/2002 | Hogenkamp et al. |
| 6,437,177 B1 | 8/2002 | Warpehoski et al. |
| 6,453,795 B1 | 9/2002 | Eicher et al. |
| 6,528,529 B1 | 3/2003 | Brann et al. |
| 6,573,278 B2 | 6/2003 | Mittendorf et al. |
| 6,610,711 B2 | 8/2003 | Armer et al. |
| 6,737,418 B2 | 5/2004 | Hogenkamp et al. |
| 7,476,756 B2 | 1/2009 | Almario-Garcia et al. |
| 7,585,881 B2 | 9/2009 | Edwards et al. |
| 7,595,397 B2 | 9/2009 | Zindell et al. |
| 7,776,897 B2 | 8/2010 | Murakami et al. |
| 7,928,123 B2 | 4/2011 | Berry et al. |
| 7,935,715 B2 | 5/2011 | Berry et al. |
| 8,048,899 B2 * | 11/2011 | Bartolozzi et al. ............ 514/363 |
| 8,173,638 B2 | 5/2012 | Berry et al. |
| 8,178,568 B2 | 5/2012 | Regan et al. |
| 2002/0099035 A1 | 7/2002 | Sandanayaka et al. |
| 2004/0067999 A1 | 4/2004 | Block et al. |
| 2004/0242913 A1 | 12/2004 | Ducray et al. |
| 2005/0059663 A1 | 3/2005 | Martin et al. |
| 2005/0182108 A1 | 8/2005 | Carson et al. |
| 2006/0061726 A1 | 3/2006 | Okuyama |
| 2006/0079557 A1 | 4/2006 | Dolle et al. |
| 2007/0021403 A1 | 1/2007 | Abouabdellah et al. |

(Continued)

FOREIGN PATENT DOCUMENTS

CH 312963 A 3/1956

(Continued)

OTHER PUBLICATIONS

Yokoyama, M. et al., "A regioselective synthesis of 3 5 disubstituted isoxazoles". Journal of the Chemical Society Perkin Transactions I, No. 1, 1986, pp. 67-72, ISSN: 0300-922X, pp. 68,69, compounds 6A, 14A.

Yordanova, K. et al. "New method for the synthesis of 2,4-disubstituted morpho-lines". Chemical Abstracts, vol. 97, No. 17, Oct. 25, 1982, Columbus, Ohio, USA Chemical Abstracts, vol. 97, No. 17, Oct. 25, 1982, Columbus, Ohio, vol. 115, No. 7, pp. 2635-2642.

Zhang, B. and Breslow, R., "Ester Hydrolysis by a Catalytic Cyclodextrin Dimer Enzyme Mimic with a Metallobipyridyl Linking Group", J. Am. Chem. Soc., 1997, vol. 119, p. 1676.

Zimmer, A. et al., "Increased mortality, Hypoactivity, and hypoalgesia in cannabinoid CB1 receptor knockout mice", Proc. Natl. Acad. Sci. USA, 1999, vol. 96, p. 5780.

(Continued)

Primary Examiner — Susannah Chung
(74) Attorney, Agent, or Firm — Michael P. Morris; Anthony P. Bottino

(57) ABSTRACT

Compounds of formula (I)

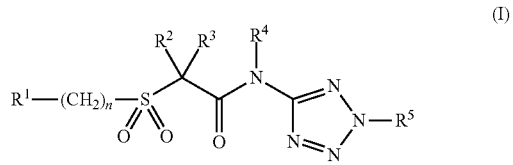

are disclosed. Compounds according to the invention bind to and are agonists, antagonists or inverse agonists of the CB2 receptor, and are useful for treating inflammation. Those compounds which are agonists are additionally useful for treating pain.

11 Claims, 2 Drawing Sheets

U.S. PATENT DOCUMENTS

| | | | |
|---|---|---|---|
| 2007/0021430 A1 | 1/2007 | Chen et al. | |
| 2007/0093501 A1 | 4/2007 | Kubo et al. | |
| 2007/0179126 A1 | 8/2007 | Casellas et al. | |
| 2007/0191340 A1 | 8/2007 | Zindell et al. | |
| 2007/0213311 A1 | 9/2007 | Li et al. | |
| 2008/0039464 A1 | 2/2008 | Berry et al. | |
| 2008/0064690 A1 | 3/2008 | Atkinson et al. | |
| 2008/0081342 A1 | 4/2008 | Fung | |
| 2008/0081822 A1 | 4/2008 | Berry et al. | |
| 2009/0163545 A1 | 6/2009 | Goldfarb | |
| 2009/0275611 A1 | 11/2009 | Riether et al. | |
| 2010/0009964 A1 | 1/2010 | Berry et al. | |
| 2010/0029644 A1 | 2/2010 | Riether et al. | |
| 2010/0076029 A1* | 3/2010 | Bartolozzi et al. | 514/340 |
| 2010/0081644 A1 | 4/2010 | Bartolozzi et al. | |
| 2010/0261708 A1 | 10/2010 | Cirillo et al. | |
| 2010/0331304 A1 | 12/2010 | Berry et al. | |
| 2011/0071127 A1 | 3/2011 | Berry et al. | |
| 2011/0071196 A1 | 3/2011 | Bartolozzi et al. | |
| 2011/0124696 A1 | 5/2011 | Regan et al. | |
| 2011/0130431 A1 | 6/2011 | Berry et al. | |
| 2011/0136869 A1 | 6/2011 | Bartolozzi et al. | |
| 2011/0190256 A1 | 8/2011 | Cirillo et al. | |
| 2011/0312932 A1 | 12/2011 | Bartolozzi et al. | |
| 2011/0312944 A1 | 12/2011 | Bartolozzi et al. | |
| 2012/0010184 A1 | 1/2012 | Bartolozzi et al. | |
| 2012/0015988 A1 | 1/2012 | Hickey et al. | |
| 2012/0071529 A1 | 3/2012 | Ermann et al. | |
| 2012/0142666 A1 | 6/2012 | Hickey et al. | |
| 2012/0142677 A1 | 6/2012 | Berry et al. | |

FOREIGN PATENT DOCUMENTS

| | | |
|---|---|---|
| DE | 1080563 B | 12/1957 |
| EP | 0628555 | 12/1994 |
| EP | 0929519 | 7/1999 |
| EP | 0970046 A1 | 1/2000 |
| EP | 1790641 A1 | 5/2007 |
| FR | 2866885 A1 | 9/2005 |
| FR | 2872813 A1 | 1/2006 |
| GB | 853799 A | 11/1960 |
| GB | 884258 A | 12/1961 |
| GB | 1237126 A | 6/1971 |
| JP | 61027905 U | 2/1986 |
| JP | 61027955 A | 2/1986 |
| JP | 61126071 A | 6/1986 |
| JP | 2003155285 | 5/2003 |
| WO | 9405628 | 3/1994 |
| WO | 9407607 | 4/1994 |
| WO | 9626925 A1 | 9/1996 |
| WO | 9712683 | 4/1997 |
| WO | 9712687 | 4/1997 |
| WO | 9720590 | 6/1997 |
| WO | 9746556 | 12/1997 |
| WO | 9808295 | 2/1998 |
| WO | 9811097 A1 | 3/1998 |
| WO | 9813340 | 4/1998 |
| WO | 9838163 A1 | 9/1998 |
| WO | 0008015 A2 | 2/2000 |
| WO | 0100573 | 1/2001 |
| WO | 0129007 | 4/2001 |
| WO | 0164651 | 9/2001 |
| WO | 02051806 | 7/2002 |
| WO | 02088089 A1 | 7/2002 |
| WO | 02062750 | 8/2002 |
| WO | 03037274 A2 | 5/2003 |
| WO | 03055482 | 7/2003 |
| WO | 03000807 | 12/2003 |
| WO | 04000807 | 12/2003 |
| WO | 2004014370 A2 | 2/2004 |
| WO | 2004014825 | 2/2004 |
| WO | 2004014902 A2 | 2/2004 |
| WO | 2004018433 | 3/2004 |
| WO | 2004026301 A1 | 4/2004 |
| WO | 2004029027 | 4/2004 |
| WO | 2004042351 A2 | 5/2004 |
| WO | 2004050643 | 6/2004 |
| WO | 2004060882 | 7/2004 |
| WO | 2004099200 A1 | 11/2004 |
| WO | 2004099205 | 11/2004 |
| WO | 2005027837 | 3/2005 |
| WO | 2005040355 | 5/2005 |
| WO | 2005077345 A1 | 8/2005 |
| WO | 2005077368 A2 | 8/2005 |
| WO | 2005077373 A2 | 8/2005 |
| WO | 2005085227 | 9/2005 |
| WO | 2006012227 | 2/2006 |
| WO | 2006030805 A1 | 3/2006 |
| WO | 2006060461 | 6/2006 |
| WO | 2006074445 A2 | 7/2006 |
| WO | 2006080040 | 8/2006 |
| WO | 2006095159 | 9/2006 |
| WO | 2006100502 | 9/2006 |
| WO | 2006117461 A2 | 11/2006 |
| WO | 2007020502 A2 | 2/2007 |
| WO | 2007054770 A2 | 5/2007 |
| WO | 2007070760 | 6/2007 |
| WO | 2007070760 A2 | 6/2007 |
| WO | 2007080382 A1 | 7/2007 |
| WO | 2007102059 | 9/2007 |
| WO | 2007118041 A1 | 10/2007 |
| WO | 2007140385 A2 | 12/2007 |
| WO | 2008014199 A2 | 1/2008 |
| WO | 2008023159 A1 | 2/2008 |
| WO | 2008039645 A1 | 4/2008 |
| WO | 2008048914 A1 | 4/2008 |
| WO | 2008064054 A2 | 5/2008 |
| WO | 2008098025 A1 | 8/2008 |
| WO | 2008104994 A2 | 9/2008 |
| WO | 2009055357 A1 | 4/2009 |
| WO | 2009061652 A1 | 5/2009 |
| WO | 2009077533 A1 | 6/2009 |
| WO | 2009105509 A1 | 8/2009 |
| WO | 2009140089 A2 | 11/2009 |
| WO | 2010005782 A1 | 1/2010 |
| WO | 2010036630 A2 | 4/2010 |
| WO | 2010036631 A2 | 4/2010 |
| WO | 2010077836 A2 | 7/2010 |
| WO | 2010096371 A2 | 8/2010 |
| WO | 2010147791 A1 | 12/2010 |
| WO | 2010147792 A2 | 12/2010 |
| WO | 2011037795 | 3/2011 |
| WO | 2011088015 A1 | 7/2011 |
| WO | 2011109324 A1 | 9/2011 |
| WO | 2012012307 A1 | 1/2012 |

OTHER PUBLICATIONS

Zindell, R. et al., "Discovery of a novel class of CB2 agonists". General Poster Session. The 235th ACS National Meeting, New Orleans, LA, USA. Apr. 6-10, 2008.

Ibrahim, M. M. et al., "Activation of CB2 cannabinoid receptors by AM1241 inhibits experimental neuropathic pain: Pain inhibition by receptors not present in the CNS", PNAS, 2003, vol. 100, No. 18, p. 10529.

Iddon, B. et al., "Condensed thiophen ring systems. Part SVII. A new synthesis of 10H-indeno[1,2-b][1] benzothiophen". Journal of the Chemical Society. Perkin Transactions 1, Chemical Soceity. Letchworth, GB. vol. 21, Jan. 1, 1974, pp. 2505-2508. ISSN: 0300-922X, p. 2506; compound 8.

Iddon, B. et al., "Polyhalogenoaromatic Compounds. Part 42. C N.m.r. Spectra of Polyhalogeno-pyridines and—pyrimidines". XP009094360, Ramage Laboratories, Dept of Chemistry and Applied Chemistry, University of Salford, Salford M5 4WT, Journal of the Chemical Society, Perkin Transactions 1, 1980, p. 1370.

Igarashi, J. et al., "Improved synthesis of quinine alkaloids with the Teoc protective group". Tetrahedron letters, Elsevier, Amsterdam, vol. 46, No. 37, 2005, pp. 6381-6384.

Ishii, K. et al., "Smiles Rearrangement of 2-(1-Methyl-1H-tetrazol-5-ylthio)acetamides and their Sulfonyl Derivatives". XP009094359, Chem. Pharm. Bull. 39(12) 3331-3334 (1991).

Johansen et al., AMPA Receptor Agonists: Resolution, Configurational Assignment, and Pharmacology of (+)-(S)-and (−)-(R)-2-Amino-3-(3-Hydroxy-5-(2-Pyridyl) Isoxazol-4-yl)Propionic Acid (1-Py-AMPA); Chirality, New York, 1997, vol. 9, No. 3, pp. 274-280.

Katoh, A., et al., "Synthesis of 6-(Bromoacetyl)Amino-2,3-Dimorpholino-Quinoxaline and Application to a new Fluorescence Derivatization Reagent of Fatty Acids for the High-Performance Liquid Chromatographic Analysis", Heterocycles, 1999, vol. 50, No. 1, p. 299.

Katz, L., et al., "Hydrazine Derivatives. II. Ortho-Mercapto-Pyridinecarbohydrazides", Contribution from Schenley Laboratories, Inc., 1953, p. 711.

Klein, T. W., et al., "The Cannabinoid system and immune modulation", J. Leukocyte Biology, 2003, vol. 74, p. 486.

Kolehmainen, E. et al., "a-Phenylsulfonyl-N-arylacetamides (a-phenylsulfonylacetanilides): H, C and N NMR spectral characterization". XP002465784, Magnetic Resonance in Chemistry, 2000, 38: 384-385.

Krutosikova, A. et al., "Furan derivatives. LV. Preparation of 5-aryl-2-furfuryl phenyl and 5-aryl-2-furfuryl 4-tolyl sulfones". Chemick Zvesti—Chemical Papers, Veda Bratislava, SK. vol. 28, Jan. 1, 1974, pp. 414-417, ISSN: 0366-6352, p. 414, compounds I-IX.

Lambeng, N. et al., "Discovery of a Novel Piperidinyl-Sulfonyl Benzoic Ester, Active as CB1 Agonist" POSTER. 231st ACS National Meeting, Atlanta, GA. Mar. 26-30, 2006.

Lesser, R. et al. "Homo-?-oxythionaphthene (4-Ketoisothiochromane". Charlottenburg, Industrial Chemistry Laboratory of the Institute of Technology, 1923, pp. 1642-1648.

Lutz, R. E. et al., "Antimalarials. Some piperazine derivatives". Journal of Organic Chemistry, vol. 12, 1947, pp. 771-775.

Mahmoud, A. M. et al., "Synthesis and Biological Activity of Some new 2-(N-Substituted Carboxamidomethyl Thio)-Naphth[1,2-d]Oxazoles-Part V". XP002068972, J. Indian Chem. Soc., vol. LIX, May 1982, pp. 675-677.

Malan Jr., T. P., et al., "CB2 cannabinoid receptor-mediated peripheral antinociception", PAIN, 2001, vol. 93, p. 239.

Markley, L. D., et al., "Antipicornavirus activity of substituted Phenoxybenzenes and Phenoxypyridines", J. Med. Chem., 1986, vol. 29, p. 427.

Marx, I. E. et al., "Discovery of a-amidosulfones as potent and selective agonists of CB2: Synthesis, SAR, and pharmacokinetic properties". Bioorganic and Medicinal Chemistry Letters, 2008. In press, accepted manuscript.

Messinger, P., "Sulfones via Mannich bases" Archly der Pharmazie, 1973, vol. 306, No. 8, pp. 603-610, ISSN: 0365-6233. p. 607, compounds 28A-29C.

Miroshnikova, O.V. et al., "Structure-activity relationships in the series of eremomycin carboxamides". Journal of Antibiotics, vol. 53, No. 3, 2000, pp. 286-293.

Miyano, S, et al., "Kinetic Resolution of Racemic b-Hydroxy Amines by Enantioselective N-Oxide formation". Journal of Organic Chemistry, 1985, vol. 50, pp. 4350-4360.

Mohler, et al., "Nonsteroidal tissue selective androgen receptor modulators: a promising class of clinical candidates" University of Tennessee Health Science Center, Expert Opinion of Therapeutic Patents; Nov. 2005, vol. 15, No. 11, pp. 1565-1585.

Nackley, A. G., et al., "Selective Activation of Cannabinoid CB2 Receptors Suppresses Spinal FOS Protein Expression and Pain Behavior in a rat Model of Inflammation", Neuroscience, vol. 119, 2003, p. 747.

Office Action from the EPO for 09-0388 dated Mar. 22, 2010.

Pollard, C. B. et al., "Some amides of piperazines". Journal of American Chemical Society, vol. 75, 1953, p. 491.

Revesz, L. et al., "Novel CCR1 antagonists with oral activity in the mouse collagen induced arthritis". Bioorganic and Medicinal Chemistry Letters, vol. 15, 2005, pp. 5160-5164.

Sakuraba, S, et al., "Efficient asymmetric hydrogenation of a-amino ketone derivatives. A highly enantioselective synthesis of phenylephrine, levamisole, carnitine and propranolol". Chemical and Pharmaceutical Bulletin, Pharm. Society of Japan, 1995, vol. 43, No. 5, pp. 738-747.

Schaefer, H. et al. "On the Synthesis of 4-aminoquinolines and -quinolinones-(2) from Anthranilonitrile" Chemistry Department of the Technical University of Dresden, Journal for Practical Chemistry, vol. 321, No. 4, 1979, pp. 695-698.

Seidel M. C. et al., "Reaction of Substituted 2-carbethoxyacetyl-aminopyridines and similar compounds with triethyl orthoformate and zinc chloride". Rohm and Haas Company, Spring House, Pennsylvania 19477, 1989.

Sharkey, K. A. et al., "CB2 cannabinoid receptors: new vistas", The first International Conference devoted to studies of the CB2 cannabinoid receptor. Banff, Alberta, Canada, May 31-Jun. 3, 2007.

Sisko, J. et al., "An investigation of imidazole and oxazole synthesis using aryl-substituted TosMIC reagents". The Journal of Organic Chemistry, vol. 65, No. 5, Mar. 10, 2000, pp. 1516-1624, ISSN: 022-3263, p. 1523, table 5, compound 69.

Smith, S. R., et al., "The anti-inflammatory activities of cannabinoid receptor ligands in mouse peritonitis models", Eur. J. Pharmacology, 2001, vol. 432, p. 107.

Strating, J., et al. "Nucleophilic Additions to Bis-Tertiobutyl Sulfonyl Acetylene (Properties of the sulfonyl group XLIV 1)". University of Groningue, Organic Chemistry Laboratory, 1954, pp. 709-716.

Swanson, D. M. et al., "Identification and biological evaluation of 4-*(3-trifluoromethylpyridin-2-yl)piperzine-1-carboxylic acid (5-trifluoromethylpyridin-2-yl)amide, a high affinity TRPV1 (VR1) vanilloid receptor antagonist". Journal Med. Chem, 2005, 48, pp. 1857-1872.

Tegley, et al., "Discovery of Novel Hydroxy-Thiazoles as HIF-alpha Prolyl Hydroxylase Inhibitors: SAR, Synthesis, and Modeling Evaluation," Bioorganic & Medicinal Chemistry Letters, Pergamon, Elsevier Science, GB, vol. 18, No. 14, 2008, pp. 3925-3928.

Todorova, T. R., et al "Ring-enlargement and ring-opening reactions of 1,2-thiazetidin-3-one 1,1,-dioxides with ammonia and primary amines as nucleophiles". Helvetica Chimica Acta, vol. 82, 1999, pp. 354.

Troeger, J. et al., "Regarding sulfonated Butyric Acids". From the Laboratory for Pharmaceutical and Synthetic Chemistry of the Braunschweig Institute of Technology.1991, 40, 506.

Troeger, J. and Uhde, R., "Ueber sulfonirte buttersauren", J. Prakt. Chem., 1899, 1991, vol. 59, p. 320.

Tweit, R. C., et al., "Synthesis of Antimicrobial Nitroimidazolyl 2-Sulfides, -Sulfoxides, and -Sulfones". Dept. of Chemical and Biological Research, Searle Laboratories, Chicago, IL, USA, Mar. 29, 1973, pp. 1161-1169.

U.S. Appl. No. 13/022,866, filed Feb. 8, 2011, Inventor: Angela Berry.

U.S. Appl. No. 13/037,422, filed Mar. 1, 2011, Inventor: Monika Ermann.

Ueda, Y., et al., "Involvement of cannabinoid CB2 receptor-mediated response and efficacy of cannabinoid CB2 receptor inverse agonist, JTE-907, in cutaneous inflammation in mice", Eur. J. Pharmacology, 2005, vol. 520, p. 164.

Van Sickle, M. D., et al., "Identification and Functional Characterization of Brainstem Cannabinoid CB2 receptors", Science, 2005, vol. 310, p. 329.

Venkov, A.P. et al., "A new synthesis of 1,2,3,40tetrahydro-2-methyl-4-phenylisoquinolines". Dept of Chemistry, University of Plovdiv, Bulgaria, pp. 253-255, Mar. 1990.

Vogtle, M. M. et al., "An efficient protocol for the solid-phase synthesis of malondiamides". Molecules, 2005, 10, pp. 1438-1445. XP002481324.

Walker, G.N. et al., "Synthesis of varied heterocyclic and substituted aryl alkyl secondary amines, related Schiff bases, and amides". Journal of Medicinal Chemistry, vol. 9, 1966, pp. 624-630.

Wang, Y. et al., "Rapid and efficient synthesis of 1,2,4-oxadiazoles utilizing polymer-supported reagents under microwave heating". Organic Letters, vol. 7, No. 5, Mar. 3, 2005, pp. 925-928, ISSN: 1523-7060, p. 927, compounds 14,15.

Watson, R. J., et al., "An enantioselective synthesis of sulphonamide hydroxamic acids as matrix metalloproteinase inhibitors", Pergamon, Tetrahedron Letters 43 (2002) 683-685.

Written Opinion of International Searching Authority for PCT/US2009/042665 Dec. 11, 2009.

Yang, G. et al., "Synthesis and Bioactivity of Novel Triazolo [1,5-a]Pyrimidine Derivatives[3]". XP002465786, Heteroatom Chemisry, vol. 12, No. 6, 2001, p. 491-496.

Abstract in English for JP 61-027905, Feb. 7, 1986, and WO199626925, Sep. 1996, Derwent Abstract.

Abstract in English for JP 61-027955, Feb. 7, 1986, Derwent.
Abstract in English for JP2003155285, May 27, 2003, Inventor: T. Makoto.
Anisimov, A. V. et al., "Synthesis of Sulfonyl and Sulfenyl Derivatives of Pyridine and 1,2,4-Triazole". Russian Journal of Organic Chemistry, 2006, vol. 42, No. 6, pp. 918-921.
Aranapakam, V. et al., "Synthesis and Structure—Activity Relationship of a-Sulfonylhydroxamic Acids as Novel, Orally Active Matrix Metalloproteinase Inhibitors for the treatment of Osteoarthritis", J. Med. Chem., 2003, vol. 46, p. 2361.
Aranapakam, V. et al., "Synthesis and Structure—Activity relationship of n-Substituted 4-Arylsulfonylpiperidine-4-hydroxamic Acids as Novel, Orally Active matrix Metalloproteinase Inhibitors for the treatment of Osteoarthritis", J. Med. Chem., 2003, vol. 46, p. 2376.
Aranapakam, V., et al., "Synthesis and Structure—Activity relationships of 4-alkynyloxy Phenyl Sulfanyl, Sulfinyl, and Sulfonyl Alkyl Hydroxamates as Tumor Necrosis Factor-a Converting Enzyme and Matrix Metalloproteinase Inhibitors", J. Med. Chem., 2004, vol. 47, p. 6255.
Arevalo-Martin, A. et al., "Therapeutic Action of Cannabinoids in a Murine model of Multiple Sclerosis", J. of Neuroscience, 2003, vol. 23, No. 7, p. 2511.
Atwell, G. J. et al., "Relationships between Structure and Kinetics of Cyclization of 2-Aminoaryl Amides: Potential Prodrugs of Cyclization-Activitated Aromatic Mustard"., XP-002465787, J. Med. Chem, 1994, 37, 371-380.
Audouze, K. et al., "New series of morpholine and 1,4-oxazepane derivatives as dopamine D4 receptor ligands. Synthesis and 3D-QSAR model." J. Med. Chem, vol. 47, No. 12, pp. 3089-3104, 2003.
Bair, K. W. et al., "(1-pyrenylmethyl)amino alcohols, a new class of antitumor DNA intercalators. Discovery and intial amine side chain structure-activity studies". Jornal of Medicinal Chemistry, vol. 33, 1990, pp. 2385-2393.
Baker, D. et al., "Cannabinoids control spasticity and tremor in a multiple sclerosis model", Nature, 2000, vol. 404, p. 84.
Baltzly, R. et al., "The preparation of N-mono-substituted and unsymmetrically disubstituted piperzines". Journal of American Chemical Society, vol. 66, 1944, pp. 263-265.
Baltzly,R. et al., "Unsymmetrically substituted piperazines. V. Piperazine ureas". The Journal of the American Chemical Society, vol. 76, 1954, pp. 1165-1166.
Balzarini, J. et al., "Antiretroviral activity of semisynthetic derivatives of glycopeptide antibiotics". J. Med. Chem., 2003, vol. 46, No. 13, pp. 2755-2764.
Binisti, C. et al., "Structure-Activity relationships in platelet-activating factor (PAF). 11-From PAF-antagonism to phospholipase A2 inhibition: syntheses and structure-activity relationships in 1-arylsulfamido-2-alkylpiperazines", Eur. J. Med. Chem., 2001, vol. 36, p. 809.
Brown, P. J. et al., "A Ureido-Thioisobutyric Acid (GW9578) Is a Subtype-Selective PPARa Agonist with Potent Lipid-Lowering Activity", J. Med. Chem. 1999, vol. 42, p. 3785.
Bruche, L. et al., "1,3-Dipolar Cycloadditions of 3,5-Dichloro-2,4,6-trimethylbenzonitrile Oxide to Phenylsulfonylallenes". Journal of Organic Chemistry, vol. 50, 1985, pp. 3206-3208, p. 3206, compounds 5a and 5b.
Buckley, N. E. et al., "Immunomodulation by cannabinoids is absent in mice deficient for the cannabinoid CB2 receptor", Eur. J. Pharmacology, 2000, vol. 396, p. 141.
Caplus—1990:497413, Zara-Kaczian, Acta Chimica Hungarica, 1989.
Caplus—RN 112298-90-5 (Tommasi), retrieved from CAPLUS on Jan. 2, 2009.
Caplus—RN 262371-16-4 (Organ), retrieved from CAPLUS on Jan. 2, 2009.
Caplus—RN 57992-82-2 (Babayan), retrieved from CAPLUS on Jan. 2, 2009.
Cartwright, D., et al., "Abnormal Nucleophillic substitution in 3-trichloromethylpyridine, its N-oxide and 3,5-Bis(trichloromethyl)pyridine". Tetrahedron, Elsevier Science Publishers, Amsterdam, vol. 51, No. 47, 1995, pp. 12791-12796.

Chang, M. Y. et al, "Reaction of different a-sulfonyl acetamides with methyl acrylate". Tetrahedron 58 (2002) p. 5075-5080.
ChemAbstract: 246020-62-2 registry copyright ACS on STN, entered 1999. Chemcats.
ChemAbstracts, Ukraine. Order Nos. T6110295, T5962700, T5962703 abstract and "Enamine Screening Library", Jan. 1, 2009, Enamine, 23 Alexandra Matrosova St., 01103 Kiev, Ukraine.
ChemAbstracts: 693218-49-4 and 402562-90-7. 2004.
Chen, D. et al., "Preparation, properties, and synthetic potentials of novel boronates in a flourous version (flourous boronates)". Organic Letters, vol. 4. No. 6, 2002, pp. 1003-1005.
Clark, N. G. et al., "The Fungicidal Activity of Substituted Acetanilides and Related Compounds". Biochemical Journal, 1953, vol. 55, p. 839-851.
Cockcroft, X. L. et al., "Phthalazinones 2: optimization and synthesis of novel potent inhibitors of ply(ADP-ribose) polymerase". Bioorganic & Medicinal Chemistry Letters, 16, 2006, pp. 1040-1044.
Dav, Jr., R. A. et al., "Polarography of phenyl 2-thienyl and 2,2'-dithienyl ketones". 1953.
El-Hawash, S. A. M., et al., "Synthesis and invitro-Anticancer and Antimicrobial Evaluation of Some Novel Quinoxalines Derived from 3-Phenylquinoxaline-2(1H)-thione". Arch. Pharm. Chem. Life Sci, 2006, 339, p. 437-447.
EP Office Action for Case 09-0388 dated Mar. 22, 2010.
Ermann, M. et al., "Arylsulfonamide CB2 receptor agonists: SAR and optimization of CB2 selectivity", Bioorganic and Medicinal Chemistry Letters 18 (2008) 1725-1729.
Ermann, M., et al., Moscone Conv.Ctr. "Discovery of a novel class of CB2 receptor agonists". Presented at the Cambridge Healthcare Institute's 15th International Molecular Medicine Tri-Conference, Moscone Convention Center, San Francisco, CA, USA. Mar. 25-28, 2008.
Ermann, M., et al., UK, "Discovery of a novel class of CB2 receptor agonists". Presented at the 14th SCI-RSC Medicinal Chemistry Symposium, Churchill College, Cambridge, UK, Sep. 23-26, 2007.
Evans, W. J. et al., "A Rearrangement of Carbamyl-sulphones and -sulphides". Journal of the Chemical Society, 1936, p. 329-331.
Faucher, A. M. et al., "Discovery of Small-Molecule Inhibitors of the ATPase Activity of Human Papillomavirus E1 Helicase", J. Med. Chem., 2004, vol. 47, p. 18.
Field, L. et al., "Grignard Reagents of Sulfones. IV. Reactions with Nitriles, Esters and an Isocyanate". Journal of American Society, vol. 78, 1956, p. 4389-4394.
Field, L., et al., "Methyl p-Tolyl Sulfone", Organic Syntheses, Coll. vol. 4, p. 674, 1963; vol. 38, p. 62, (1958).
Fringuelli, F. et al., "Solvent-Free Al(OTi)3-catalyzed aminolysis of 1,2-Epoxides by 2-picolylamine: a key step in the synthesis of ionic liquids". Journal of Organic Chemistry, vol. 69, 2004, pp. 7745-7747.
Gao, M., et al "Synthesis of new carbon-11 labeled benzoxazole derivatives for PET imaging of 5-HT3 receptor", Science Direct, European Journal of Medicinal Chemistry, 43, 2008, pp. 1570-1574.
Gartst, M., et al., "Hydroformylation of bisolefinic amine derivatives catalyzed by cobalt and rhodium". Journal of Organic Chemistry, vol. 46, 1981, pp. 4433-4438.
Gavalda, et al N-Sulfonyl hydroxamate derivataves as inhibitors of class II fructose-1, 6-diphosphate aldolase, Bioorganic & Medicinal Chemistry Letter, 2005, vol. 15, No. 24, pp. 5375-5377.
Goldschmidt,St. et al., "Biphenyl derivatives II. Basic 4-Biphenyl Compounds". Receuil Travaux Chimiques Des Pays-Bas, vol. 69, 1950, pp. 1109-1117.
Grothe, V. W. et al. "Effect of Potassium Sulfhydrate etc. on Chloroacetylanilides". Archly der Pharmazie (Weinheim), vol. 238, 1980, p. 600-614.
Hanus, L. et al., "HU-308: A specific agonist for CB2, a peripheral cannabinoid receptor", PNAS, 1999, vol. 96, No. 25, p. 14228.
Herndon, J. L. et al., "Ketanserin analogues. Structure-affinity relationships for 5-HT2 and 5-HT1c serotoninin receptor binding". J. Med. Chem, 1992, vol. 35, No. 26, pp. 4903-4910.
Huang, X. et al., "A Novel Synthesis of Sulfones via the O,O-Diethylphosphorotellurite Ion-assisted Coupling of Arenesulfonyl Chlorides with Active Halides". Synthetic Communications, 20(15), 2291-2291-2295 (1990).

Beilstein Database—Beilstein Registry No. 1084348. CAS Registry No. 6125-38-8. Beilstein Institute for Organic Chemistry. 1966, Abstract.

Beilstein Database—Beilstein Registry No. 1179643. CAS Registry No. 54890-73-2. Beilstein Institute for Organic Chemistry. 1974, Abstract.

Beilstein Database—Beilstein Registry No. 5396840. CAS Registry No. 54890-82-3. Beilstein Institute for Organic Chemistry. 1974, Abstract.

Beilstein Database—Beilstein Registry No. 5398283. CAS Registry No. 68558-02-01. Beilstein Institute for Organic Chemistry. 1978, Abstract.

Beilstein Database—Beilstein Registry No. 857451. CAS Registry No. 37901-58-9. Beilstein Institute for Organic Chemistry. 1972, Abstract.

Carenzi, A, et al., "New Isoxazole Derivatives Provided with Antihypertensive Activity". Arzneimittel-Forschung, vol. 39, No. 6, 1989, p. 624-646.

Chem Abstract—Accession No. 126:89390, Abstract of JP8311026, Kumaiai Chemical Industry Co., Nov. 26, 1996.

Hadjipavlou-Litina, D. et al., "Thiazolyl-N-Substituted Amides: A group of effective anti-inflammatory agents with potential for local anesthetic properties. Synthesis, Biological Evaluation, and a QSAR Approval." Drug Development Research, Vo. 48, 1999, p. 53-60.

International Search Report and Written Opinion for PCT/US2011/026574 mailed Apr. 11, 2011.

Kano, S. et al., "Formation of Some Heterocycles through Ring Transformation of 1-Arylaxetidin-2-Ones." Heterocycles, vol. 8, No. 1, Dec. 30, 1977, p. 411-416.

Sheehan, J.C. et al, The Synthesis and Reactions of Some Substitued Beta-Lactams, 1951, Journal of the American Chemical Society, 73, 1761-1765.

* cited by examiner

| Column | Waters Atlantis dC18 2.1 x100mm, 3μm column | | Flow rate | 0.6 ml/min |
|---|---|---|---|---|
| Mobile Phase | A, 0.1% Formic acid (water) B, 0.1% Formic acid (CH₃CN) | | Injection Vol | 3 μl |
| Temp. | 40°C | | Detection | 215nm (nominal) |
| Gradient | Time (mins) | % organic | | |
| | 0.00 | 5 | | |
| | 5.00 | 100 | | |
| | 5.40 | 100 | | |
| | 5.42 | 5 | | |
| | 7.00 | 5 | | |

| Column | Atlantis dC18 2.1 x 50mm, 5μm | | Flow rate | 1 ml/min |
|---|---|---|---|---|
| Mobile Phase | A, Formic acid (aq) 0.1% | | Injection Vol | 3 μl |
| | B, Formic acid (CH$_3$CN) 0.1% | | | |
| Temp. | 40°C | | Detection | 215nm (nominal) |
| Gradient | Time (mins) | % organic | | |
| | 0.00 | 5 | | |
| | 2.50 | 100 | | |
| | 2.70 | 100 | | |
| | 2.71 | 5 | | |
| | 3.00 | 5 | | |

TETRAZOLE COMPOUNDS WHICH SELECTIVELY MODULATE THE CB2 RECEPTOR

APPLICATION DATA

This application claims priority to U.S. provisional application Ser. No. 61/310,743 filed Mar. 5, 2010.

BACKGROUND OF THE INVENTION

1. Technical Field

The present invention relates to novel compounds which modulate the CB2 receptor and their use as medicaments.

2. Background Information

WO2008014199, WO2008039645 discuss the CB2 receptor, and the therapeutic uses of the CB2 receptor agonist compounds disclosed therein. It is believed that the highly selective activation of the CB2 receptor with an agonist may offer avenues of harnessing the beneficial effects while avoiding the adverse effects seen with dual CB1/CB2 cannabinoid receptor agonists (see e.g. Expert Opinion on Investigational Drugs (2005), 14(6), 695-703). It is desirable therefore to provide agonists of CB2 with minimized CB1 activity.

WO2008014199, WO2008039645 and WO 2009061652 disclose sulfone derivatives having CB2 agonist activity. The compounds of the present invention differ structurally from the above disclosed compounds, for example the present tetrazole in the formula (I) disclosed hereinbelow. Additionally, the compounds of the present invention have improved pharmaceutical properties as described herein than the compounds disclosed in the cited art.

BRIEF SUMMARY OF THE INVENTION

The present invention provides novel compounds which bind to and modulate the CB2 receptor and have lower CB1 receptor activity and in addition possess desirable properties for HLM stability, solubility and Ames. The invention also provides methods and pharmaceutical compositions for treating inflammation by way of the administration of therapeutic amounts of the compounds of the invention. Lastly, the invention provides a method and pharmaceutical compositions for treating pain by way of the administration of therapeutic amounts of the compounds of the invention.

DETAILED DESCRIPTION OF THE INVENTION

In the broadest generic embodiment 1, the invention provides compounds of the formula

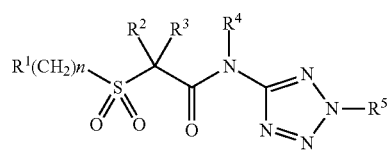
(I)

wherein:
$R^1$ is $C_{1-10}$ alkyl, $C_{1-10}$ alkoxy, $C_{3-10}$ cycloalkyl, 3-10 membered saturated heterocyclic ring or aryl each optionally independently substituted with 1-3 substituents chosen from $C_{1-4}$ alkyl, $C_{1-4}$ alkoxy, $C_{3-10}$ cycloalkyl, $C_{1-4}$ alkylsulfonyl, acyl, oxo, cyano, phenyl, hydroxyl and halogen;

$R^2$ and $R^3$ are $C_{1-4}$ alkyl or hydrogen with the proviso that both $R^2$ and $R^3$ cannot be hydrogen; or $R^2$ and $R^3$ together with the carbon atom to which they are attached form a 3- to 6-membered cycloalkyl or heterocyclic ring;

$R^4$ is hydrogen or methyl;

$R^5$ is chosen from $C_{1-10}$ alkyl, $C_{1-10}$ alkoxy, $C_{3-10}$ cycloalkyl, 3-10 membered saturated heterocyclic ring, 5-6 membered heteroaryl ring and aryl each optionally independently substituted with 1-3 substituents chosen from $C_{1-4}$ alkyl, $C_{1-4}$ alkoxy, $C_{3-10}$ cycloalkyl, $C_{1-4}$ alkylsulfonyl, acyl, oxo, cyano, hydroxyl and halogen;

n is 0, 1 or 2;

wherein any carbon atom on the formula (I) or any R substituent listed above is optionally partially or fully halogenated where possible;

or a pharmaceutically acceptable salt thereof.

In another embodiment 2, the invention provides compounds of the formula (I) according to any of the preceding embodiments described above, and wherein $R^1$ is $C_{1-5}$ alkyl, phenyl, cyclopropyl, cyclobutyl, cyclopentyl, cyclohexyl, cycloheptyl, cyclooctyl, tetrahydrofuranyl, tetrahydropyranyl, azetidinyl, piperidinyl; dioxanyl, thiomorpholinyl, 1,1-Dioxo-1λ$^6$-thiomorpholinyl, morpholinyl, pyrrolidinyl, piperazinyl, and Dihydro-2H-quinolinyl, each optionally substituted by 1-3 substituents chosen from halogen, $C_{1-4}$ alkyl, $C_{1-4}$ alkoxy and hydroxyl;

$R^2$ and $R^3$ are independently methyl, ethyl, n-propyl, isopropyl, or hydrogen with the proviso that both $R^2$ and $R^3$ cannot be hydrogen; or $R^2$ and $R^3$ together with the carbon to which they are attached form a cyclopropyl, cyclobutyl, or cyclopentyl ring;

$R^4$ is hydrogen;

$R^5$ is $C_{1-5}$ alkyl;

In another embodiment 3, the invention provides compounds of the formula (I) according to any of the preceding embodiments described above, and wherein $R^2$ and $R^3$ are methyl;

In another embodiment 4, the invention provides compounds of the formula (I) according to any of the preceding embodiments above, and wherein $R^1$ is $C_{1-4}$ alkyl, phenyl, cyclohexyl, tetrahydrofuranyl, tetrahydropyranyl or dioxanyl, each optionally substituted by 1-3 substituents chosen from halogen, $C_{1-4}$ alkyl, $C_{1-4}$ alkoxy and hydroxyl;

$R^5$ is methyl, ethyl, propyl, butyl or t-butyl;

In another embodiment 5, the invention provides compounds of the formula (I) according to any of the preceding embodiments above, and wherein $R^5$ is t-butyl.

In another embodiment 6, the invention provides compounds of the formula (I) according to any of the preceding embodiments above, and wherein the combination $R^1(CH_2)_n$— is

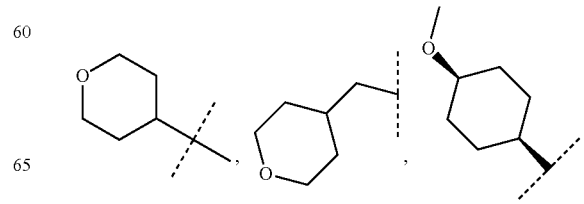

-continued

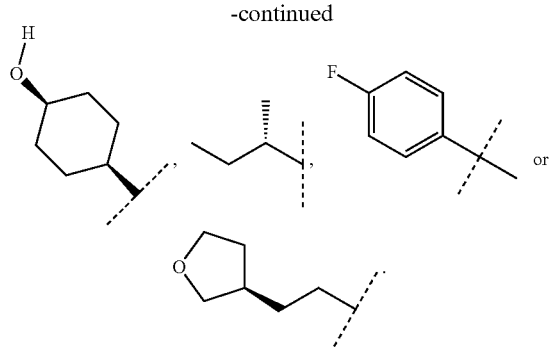

In another embodiment, the invention provides made compounds in Table I which can be made in view of the general schemes, examples and methods known in the art.

TABLE I

Structure

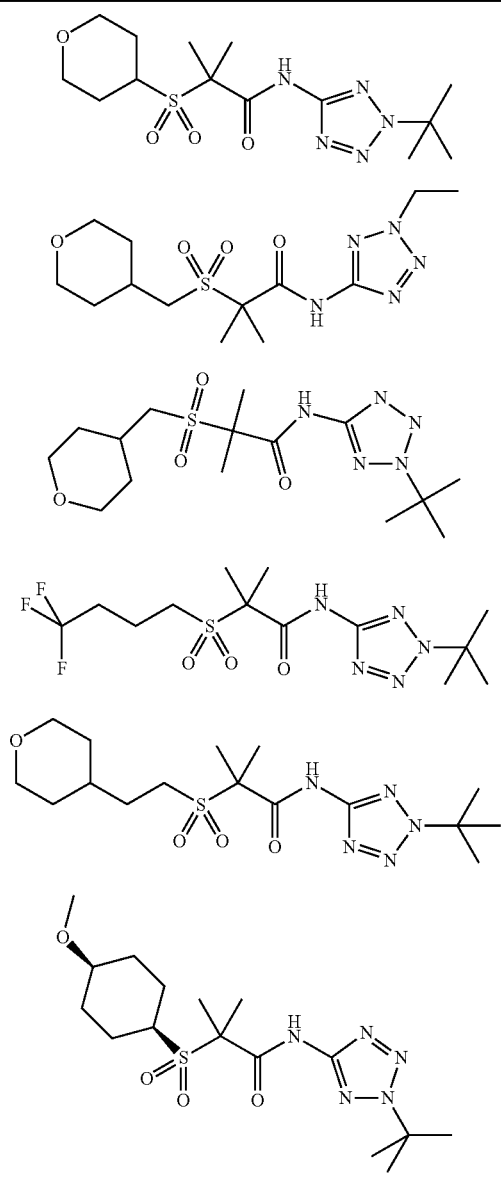

TABLE I-continued

Structure

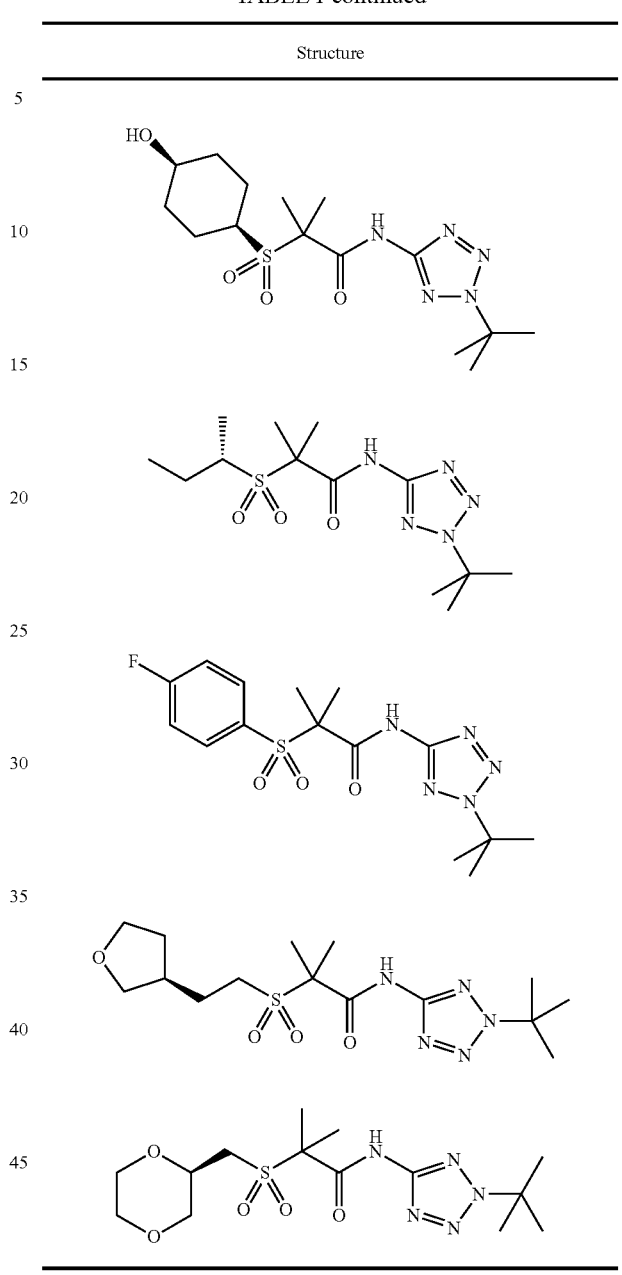

or a pharmaceutically acceptable salt thereof.

Of the above compounds, the following are preferred CB2 agonists:

TABLE II

| Compound | CB2 EC$_{50}$ (nM) | CB1 EC$_{50}$ (nM) |
|---|---|---|
|  | 21 | >20,000 |

TABLE II-continued

| Compound | CB2 EC$_{50}$ (nM) | CB1 EC$_{50}$ (nM) |
|---|---|---|
| [structure: tetrahydropyranylmethyl-sulfonyl-dimethyl-acetamido-tetrazole-t-butyl] | 50 | >50,000 |
| [structure: methoxycyclohexyl-sulfonyl-dimethyl-acetamido-tetrazole-t-butyl] | 56 | >50,000 |
| [structure: hydroxycyclohexyl-sulfonyl-dimethyl-acetamido-tetrazole-t-butyl] | 8.7 | >50,000 |
| [structure: sec-butyl-sulfonyl-dimethyl-acetamido-tetrazole-t-butyl] | 101 | >50,000 |
| [structure: 4-fluorophenyl-sulfonyl-dimethyl-acetamido-tetrazole-t-butyl] | 22 | 39,500 |
| [structure: tetrahydrofuranyl-ethyl-sulfonyl-dimethyl-acetamido-tetrazole-t-butyl] | 12 | ~50,000 |

In all the compounds disclosed hereinabove in this application, in the event the nomenclature is in conflict with the structure, it shall be understood that the compound is defined by the structure.

The invention also relates to pharmaceutical preparations, containing as active substance one or more compounds of formula (I), or the pharmaceutically acceptable derivatives thereof, optionally combined with conventional excipients and/or carriers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes the use of any compounds of described above containing one or more asymmetric carbon atoms may occur as racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of formula (I) can exist in more than one tautomeric form. The invention includes methods using all such tautomers.

All terms as used herein in this specification, unless otherwise stated, shall be understood in their ordinary meaning as known in the art. For example, "$C_{1-4}$alkoxy" is a $C_{1-4}$alkyl with a terminal oxygen, such as methoxy, ethoxy, propoxy, butoxy. All alkyl, alkenyl and alkynyl groups shall be understood as being branched or unbranched where structurally possible and unless otherwise specified. Other more specific definitions are as follows:

Carbocycles include hydrocarbon rings containing from three to twelve carbon atoms. These carbocycles may be either aromatic either aromatic or non-aromatic ring systems. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl. Certain terms for cycloalkyl such as cyclobutanyl and cyclobutyl shall be used interchangeably.

The term "heterocycle" refers to a stable nonaromatic 3-10 membered (but preferably, 5 or 6 membered) monocyclic or nonaromatic 8-11 membered bicyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure.

The term "heteroaryl" shall be understood to mean an aromatic 5-10 membered monocyclic or bicyclic ring containing 1-4 heteroatoms such as N, O and S.

Unless otherwise stated, heterocycles and heteroaryl include but are not limited to, for example azetidinyl, benzoxazolyl, benzothiazolyl, benzimidazolyl, tetrahydropyranyl, dioxanyl, tetrahydrofuranyl, oxazolyl, isoxazolyl, thiazolyl, pyrazolyl, pyrrolyl, imidazolyl, thienyl, thiadiazolyl, triazolyl, thiomorpholinyl, 1,1-Dioxo-1$\lambda^6$-thiomorpholinyl, morpholinyl, pyridinyl, pyrimidinyl, pyridazinyl, pyrazinyl, triazinyl, pyrrolidinyl, piperidinyl, piperazinyl, purinyl, quinolinyl, Dihydro-2H-quinolinyl, isoquinolinyl, quinazolinyl, indazolyl, thieno[2,3-d]pyrimidinyl, indolyl, isoindolyl, benzofuranyl, benzopyranyl and benzodioxolyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in defintions such as but not limited to: alkoxycarbonyl, acyl, amido and thioxo.

The term "aryl" as used herein shall be understood to mean aromatic carbocycle or heteroaryl as defined herein. Each aryl or heteroaryl unless otherwise specified includes it's partially or fully hydrogenated derivative. For example, quinolinyl may include decahydroquinolinyl and tetrahydroquinolinyl, naphthyl may include its hydrogenated derivatives such as tetrahydronaphthyl. Other partially or fully hydrogenated derivatives of the aryl and heteroaryl compounds described herein will be apparent to one of ordinary skill in the art.

As used herein, "nitrogen" and "sulfur" include any oxidized form of nitrogen and sulfur and the quaternized form of any basic nitrogen. For example, for an —S—$C_{1-6}$ alkyl radical, unless otherwise specified, this shall be understood to include —S(O)—$C_{1-6}$ alkyl and —S(O)$_2$—$C_{1-6}$ alkyl.

The term "halogen" as used in the present specification shall be understood to mean bromine, chlorine, fluorine or iodine, preferably fluorine. The definitions "partially or fully halogenated"; partially or fully fluorinated; "substituted by one or more halogen atoms", includes for example, mono, di or tri halo derivatives on one or more carbon atoms. For alkyl, a nonlimiting example would be —$CH_2CHF_2$, —$CF_3$ etc.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—($C_1$-$C_4$ alkyl)$_4^+$ salts.

In addition, within the scope of the invention is use of prodrugs of compounds of the formula (I). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of formula I may be made using the general synthetic methods described below, which also constitute part of the invention.

General Synthetic Methods

The invention also provides processes for making compounds of Formula (I). In all methods, unless specified otherwise, $R^1$, $R^2$, $R^3$, $R^4$, $R^5$ and n in the formulas below shall have the meaning of $R^1$, $R^2$, $R^3$, $R^4$, $R^5$ and n in Formula (I) of the invention described herein above. Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC), if desired, and intermediates and products may be purified by chromatography on silica gel and/or by recrystallization.

The examples which follow are illustrative and, as recognized by one skilled in the art, particular reagents or conditions could be modified as needed for individual compounds without undue experimentation. Starting materials and intermediates used, in the methods below, are either commercially available or easily prepared from commercially available materials by those skilled in the art. Synthetic methods disclosed in WO2008098025, WO2008014199, WO2008039645, and WO2009061652 may also be used in preparing compounds of the invention.

Compounds of Formula (I) may be synthesized by the method illustrated in Scheme 1

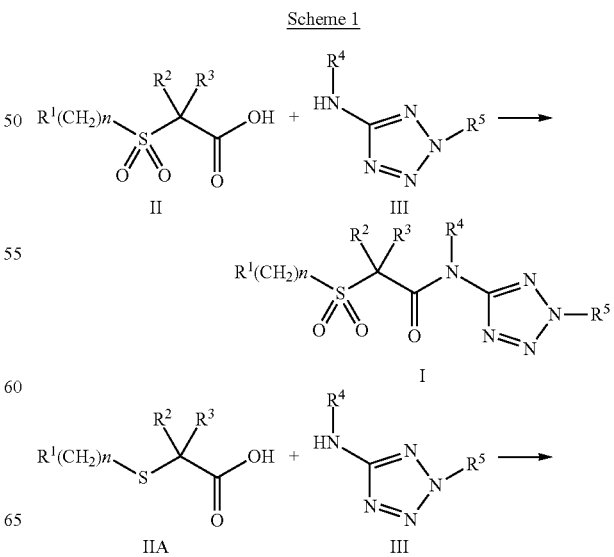

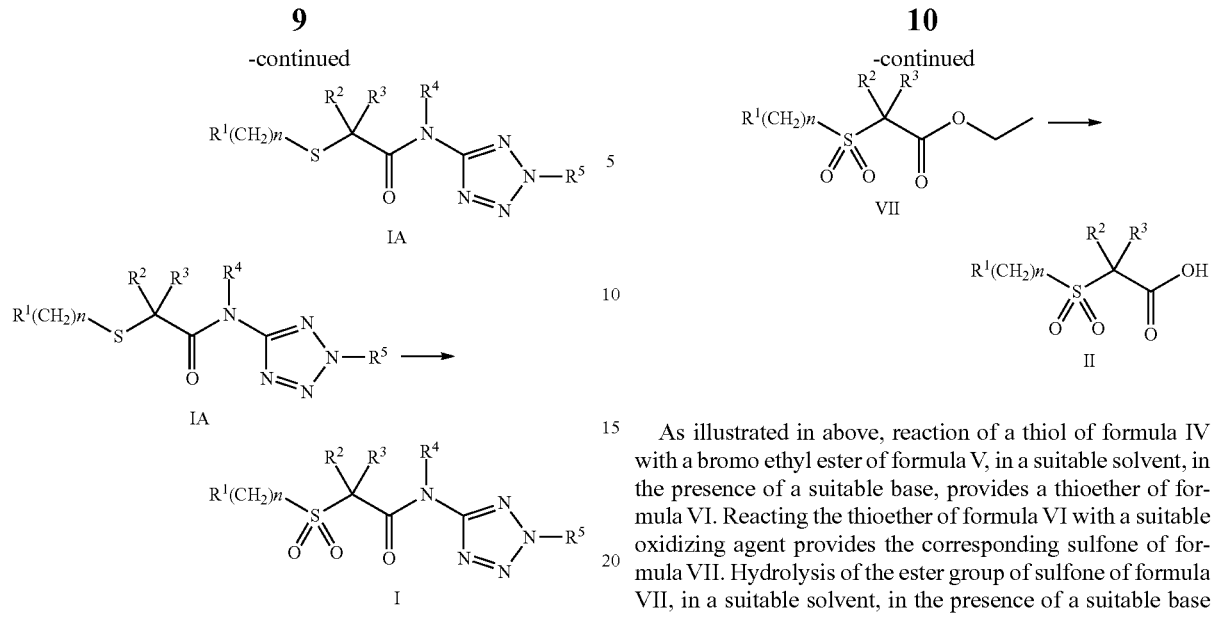

As shown in scheme 1, reacting the acid of formula II or IIA with a reagent such as thionyl chloride or oxalyl chloride, provides the acid chloride which is then reacted with an amine of formula III, in a suitable solvent, in the presence of a suitable base, to provide a compound of formula (I) or IA. Alternatively, the acid of formula II or IIA may also be coupled with an amine of formula III under standard coupling conditions, to provide a compound of formula (I) or IA. Standard peptide coupling reactions known in the art (see for example M. Bodanszky, 1984, The Practice of Peptide Synthesis, Springer-Verlag) may be employed in these syntheses. An example of suitable coupling conditions is treatment of a solution of the carboxylic acid in a suitable solvent such as DMF with EDC, HOBT, and a base such as diisopropylethylamine, followed by the desired amine.

Oxidation of a compound of formula IA, in a suitable solvent, with an oxidizing agent such as oxone, provides a compound of formula (I).

Further modification of the initial product of formula (I) by methods known in the art and illustrated in the Examples below, may be used to prepare additional compounds of this invention.

Intermediate acid II may be made by the method outlined in Scheme 2

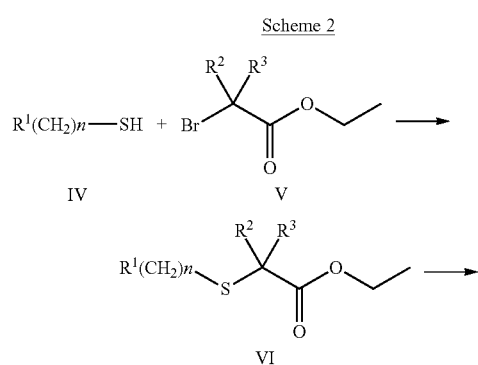

As illustrated in above, reaction of a thiol of formula IV with a bromo ethyl ester of formula V, in a suitable solvent, in the presence of a suitable base, provides a thioether of formula VI. Reacting the thioether of formula VI with a suitable oxidizing agent provides the corresponding sulfone of formula VII. Hydrolysis of the ester group of sulfone of formula VII, in a suitable solvent, in the presence of a suitable base such as lithium hydroxide, provides the corresponding acid of formula II.

Intermediate acid II may also be made by the method outlined in Scheme 3

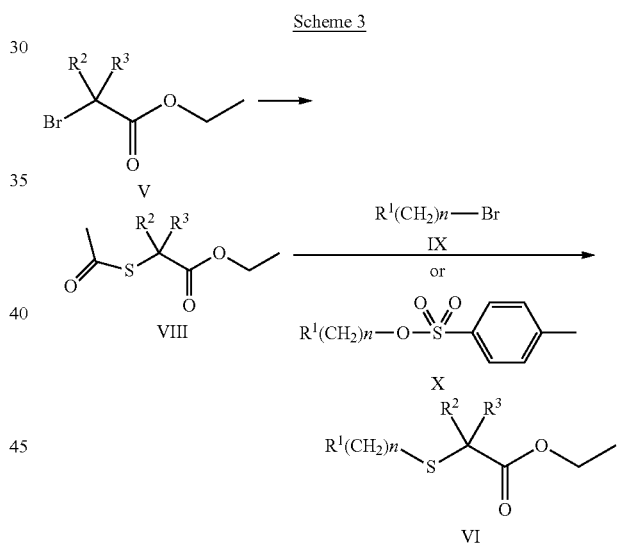

Reaction of the starting bromoester of formula V with a reagent such as potassium thioacetate, in a suitable solvent, provides a thioacetic acid ester of formula VIII. Reaction of the thioacetic acid ester VIII with a bromide of formula IX, in a suitable solvent in the presence of a suitable base, provides the corresponding sulfanyl acid ethyl ester of formula VI. Reaction of the thioacetic acid ester of formula VIII with a tosylate of formula X, in a suitable sovent, in the presence of a suitable base, provides the sulfanyl acid ethyl ester of formula VI. The sulfanyl acid ethyl ester of formula VI may be converted to intermediate acid of formula II by the sequence of steps shown in scheme 2. The sulfanyl acid ethyl ester of formula VI may be hydrolysed, under standard conditions, to provide an acid of formula IIA in scheme 1.

Intermediate acid II may be made by the method outlined in Scheme 4

Scheme 4

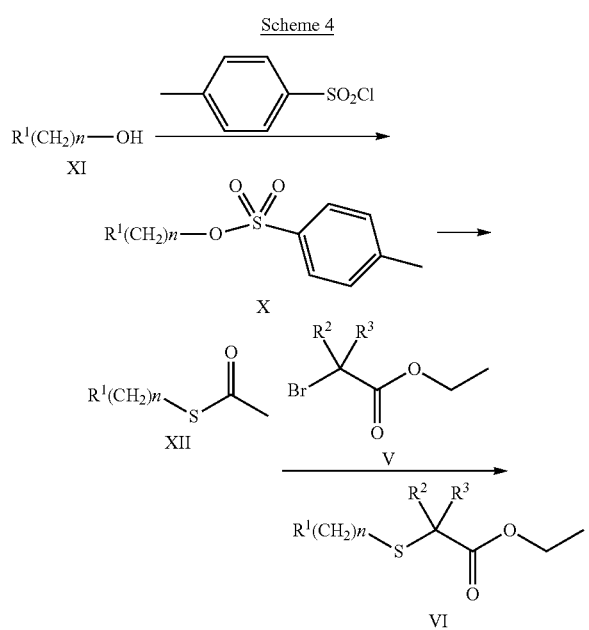

As illustrated in scheme 4, reaction of an alcohol of formula XI with p-toluenesulfonyl chloride, in a suitable solvent, in the presence of a suitable base, provides the sulfonic acid ester of formula X. Reaction of the compound of formula X with potassium thioacetate, in a suitable solvent, provides a compound of formula XII. Reaction of the intermediate of formula XII with the bromoester of formula V, in a suitable solvent, in the presence of a suitable base, provides the intermediate of formula VI which may be converted to the desired intermediate acid of formula II by the reaction sequence shown in scheme 2. Methane sulfonyl chloride may also be used in the first step instead of p-toluenesulfonyl chloride, as described in the example section.

Intermediate acid II may be prepared by the method outlined in Scheme 5

Scheme 5

R$^1$(CH$_2$)$n$—Br ⟶
IX

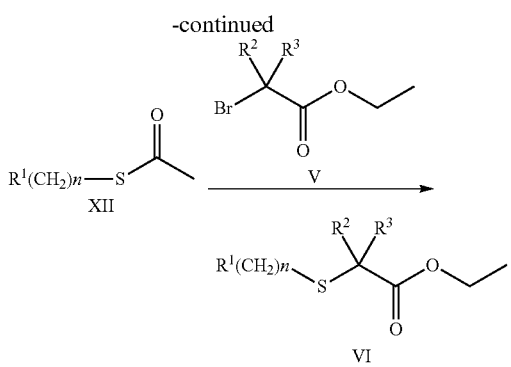

As illustrated in scheme 5, reaction of a bromo compound of formula IX with a reagent such as potassium thioacetate, in a suitable solvent, provides an acetylsulfanyl compound of formula XII. Reaction of the compound of formula XII with a bromo ethyl ester of formula V, in a suitable solvent, in the presence of a suitable base, provides a thioether of formula VI. The thioether of formula VI may be converted to the corresponding acid of formula II by the reaction sequence shown in scheme 2.

Intermediate amine III may be made by the method outlined in Scheme 6

Scheme 6

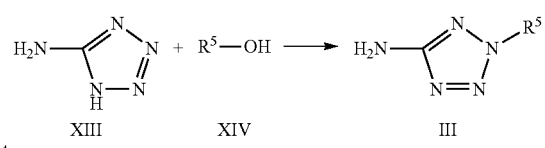

R$^4$ = hydrogen

As shown above in scheme 6, reaction of an amine of formula XIII with an alcohol of formula XIV, in a suitable solvent, in the presence of suitable reagents such as dicyclohexyl carbodiimide and cupric chloride, provides an amine of formula III, wherein R$^4$=H.

SYNTHETIC EXAMPLES

The manner in which the compounds of the invention can be made will be further understood by way of the following Examples.

Acid Method A:
Synthesis of Compound A7

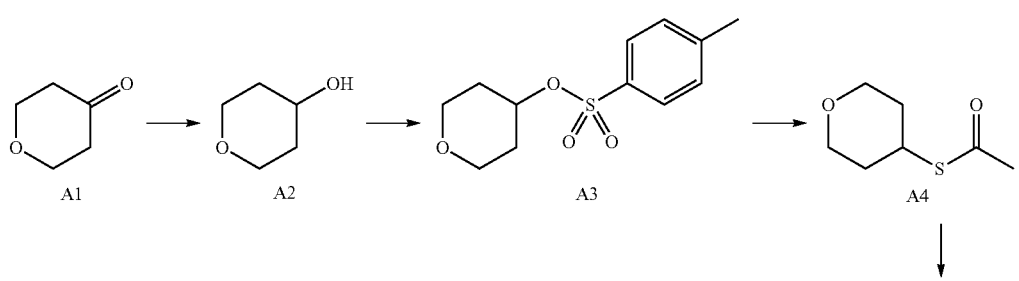

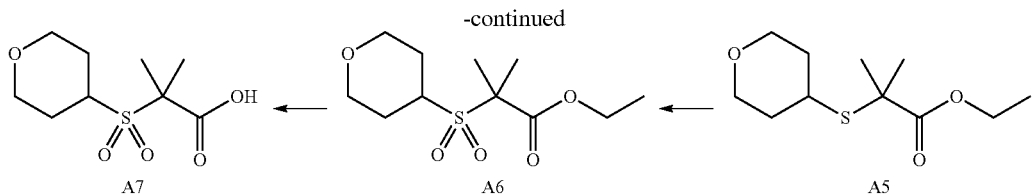

Step 1: Synthesis of Compound A2

To a solution of 75 g (0.75 mol) of compound A1 in THF (150 mL) is added a suspension of 28.4 g (0.75 mol) LiAlH$_4$ in THF (600 mL) under nitrogen atmosphere maintaining the temperature below 30° C. with the aid of an ice-bath. Then the reaction is allowed to warm to room temperature and stirred for 5 h. The reaction is quenched by addition of saturated aqueous NH$_4$Cl solution until effervescence ceased. The resulting precipitate is removed by filtration through Celite® and washed with THF (150 mL). The filtrate is concentrated under reduced pressure to afford 71.1 g of compound A2 as a pale yellow oil. Yield: 92%, $^1$H NMR (500 MHz, CHLOROFORM-d) δ ppm 1.54 (2H, m, J=13.37, 9.55, 9.55, 4.22 Hz), 1.81-1.92 (2H, m), 2.11 (1H, br. s.), 3.38-3.47 (2H, m), 3.83 (1H, tt, J=9.10, 4.38 Hz), 3.94 (2H, dt, J=11.88, 4.15 Hz)

Step 2: Synthesis of Compound A3

To a solution of 133 g (1.31 mol) of compound A2 in pyridine (1.5 L) are added 373 g (1.95 mol) of p-toluenesulfonylchloride portionwise at 10° C. After complete addition the reaction is allowed to warm to room temperature and stirred for 18 h. The reaction is poured onto a stirred mixture of aqueous HCl/ice. The resulting precipitate is isolated by filtration and dissolved in DCM (1 L). The organic layer is washed with 1M aqueous HCl solution (1 L), followed by saturated aqueous NaHCO$_3$ solution (1 L) and is then dried over Na$_2$SO$_4$. Filtration and concentration of the filtrate under reduced pressure gives 300 g of compound A3 as an orange oil. Yield: 90%, ES-MS: m/z: 257 [M+H], 279 [M+Na]

According to this procedure the following compounds are synthesized:

TABLE I

| Structure | $^1$H NMR | Yield [%] | m/z [M + H] |
|---|---|---|---|
| 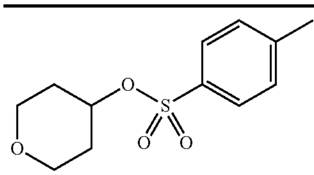 | (250 MHz, CHLOROFORM-d) δ ppm 1.66-1.96 (4 H, m), 2.45 (3 H, s), 3.47 (2 H, ddd, J = 11.76, 8.19, 3.50 Hz), 3.79-3.95 (2 H, m), 4.69 (1 H, tt, J = 8.13, 4.13 Hz), 7.35 (2 H, d, J = 8.07 Hz), 7.76-7.87 (2 H, m) | 90 | 257 |
| 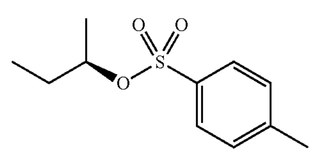 | (500 MHz, CHLOROFORM-d) δ ppm 0.83 (3 H, t, J = 7.48 Hz), 1.26 (3 H, d, J = 6.26 Hz), 1.47-1.70 (2 H, m), 2.45 (3 H, s), 4.57 (1 H, sxt, J = 6.23 Hz), 7.34 (2 H, d, J = 8.39 Hz), 7.81 (2 H, d, J = 8.24 Hz); | 62 | $[\alpha]^{25}_{578}$* |

*$[\alpha]^{25}_{578}$-2.36 (3, CCl$_4$) (lit. $[\alpha]^{25}_{578}$-10.9 (2-4, CCl$_4$), Allen et al. *J. Org. Chem*, 2003, 48, 4527-4530)

Step 3: Synthesis of Compound A4

To a solution of 300 g (1.175 mol) of compound A3 in DMF (3 L) are added 268 g (2.35 mol) potassium thioacetate, followed by a catalytic amount of NaI (0.12 g, 10 mol %) at room temperature. After complete addition, the reaction is heated to 50° C. for 20 h. The reaction mixture is partitioned between TBME (3 L) and water (3 L), the aqueous layer is extracted with TBME (2 L), then saturated with NaCl and extracted again with TBME (2×2 L). The combined organic extracts are dried over Na$_2$SO$_4$, filtered and the solvent is removed under reduced pressure to afford 153 g of compound A4. Yield: 81%; ES-MS: m/z 161 [M+H].

According to this procedure the following compounds are synthesized:

TABLE II

| Structure | ¹H-NMR | Yield [%] | m/z [M + H] |
|---|---|---|---|
| (tetrahydropyran-4-yl thioacetate) | (250 MHz, CHLOROFORM-d) δ ppm 1.47-1.98 (4 H, m), 2.30 (3 H, s), 3.41-3.74 (3 H, m), 3.88 (2 H, dt, J = 11.76, 3.86 Hz) | 86 | 161 |
| (sec-butyl thioacetate) | (500 MHz, CHLOROFORM-d + residual Et₂O) δ ppm 0.96 (3 H, t, J = 7.40 Hz), 1.29 (3 H, d, J = 7.02 Hz), 1.60 (2 H, quin, J = 7.25 Hz), 2.31 (3 H, s), 3.46-3.55 (1 H, m under Et₂O peak) | 76 | N/A |

Step 4: Synthesis of Compound A5

A solution of 153 g (0.96 mol) of compound A4 in ethanol (3.5 L) is degassed with nitrogen over 0.5 h and 125 g (2.23 mol) of KOH are added. Then a solution of 250 mL (1.68 mol) of ethyl α-bromoisobutyrate in EtOH (1 L) are added over 0.5 h, during which the temperature increased to 40° C. The reaction is stirred for 18 h at room temperature under a nitrogen atmosphere. The reaction mixture is filtered, the solid is washed with ethanol (0.5 L) and the filtrate is concentrated under reduced pressure. The crude material is dryloaded onto silica and purified by dry-flash column chromatography (silica, eluent: n-heptanes, 2-10% ethyl acetate) to afford 158 g of compound A5 as an orange-brown oil. Yield: 71%; ES-MS: m/z 233 [M+H]

According to this procedure the following compounds are synthesized

TABLE III

| Structure | ¹H NMR | Yield [%] | m/z [M + H] |
|---|---|---|---|
| (tetrahydropyranyl-S-C(CH₃)₂-CO₂Et) | (500 MHz, CHLOROFORM-d) δ ppm 1.28 (3 H, t, J = 7.17 Hz), 1.52 (6 H, s), 1.56-1.67 (2 H, m), 1.85 (2 H, dt, J = 13.35, 1.64 Hz), 3.04 (1 H, tt, J = 10.60, 4.20 Hz), 3.40-3.49 (2 H, m), 3.88 (2 H, dt, J = 11.75, 3.81 Hz), 4.14-4.20 (2 H, m) | 76 | 233 |
| (sec-butyl-S-C(CH₃)₂-CO₂Et) | (500 MHz, CHLOROFORM-d) δ ppm 0.95 (3 H, t, J = 7.40 Hz), 1.22-1.35 (7 H, m), 1.47-1.59 (7 H, m), 2.86 (1 H, sxt, J = 6.77 Hz), 4.17 (2 H, q, J = 7.12 Hz) | 100 | 205 |

Step 5: Synthesis of Compound A6

To a solution of 158 g (0.68 mol) of compound A5 in dioxane/water (4/1, 1.6 L) are added 835 g (1.35 mol) of Oxone® in portions over 50 min. The reaction mixture is stirred at room temperature for 18 h. The solid is removed by filtration and washed with dioxane (1 L). The combined filtrates are concentrated under reduced pressure. The residue is dissolved in ethyl acetate (1.5 L) and washed with water (1 L). The organic layer is dried over Na₂SO₄, filtered and the solvent is removed under reduced pressure to afford 166 g of compound A6 as a yellow oil. Yield: 92%, ES-MS: m/z 265 [M+H], 287 [M+Na].

According to this procedure the following compounds are synthesized:

TABLE IV

| Structure | ¹H-NMR | Yield [%] | m/z [M + H] |
|---|---|---|---|
| (tetrahydropyranyl-SO₂-C(CH₃)₂-CO₂Et) | (250 MHz, CHLOROFORM-d) δ ppm 1.30 (3 H, t, J = 7.08 Hz), 1.65 (6 H, s), 1.89-2.10 (4 H, m), 3.34-3.51 (2 H, m), 3.72-3.90 (1 H, m), 4.06 (2 H, dt, J = 11.69, 3.60 Hz), 4.24 (2 H, q, J = 7.16 Hz) | 90 | 265, 287 [M + Na] |

TABLE IV-continued

| Structure | $^1$H-NMR | Yield [%] | m/z [M + H] |
|---|---|---|---|
| 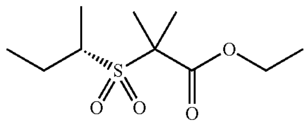 | (500 MHz, CHLOROFORM-d) δ ppm 1.05 (3 H, t, J = 7.48 Hz), 1.34 (3 H, t, J = 7.10 Hz), 1.40 (3 H, d, J = 6.87 Hz), 1.62-1.70 (7 H, m), 2.06 (1 H, ddd, J = 13.96, 7.55, 3.81 Hz), 3.54-3.63 (1 H, m), 4.27 (2 H, q, J = 7.17 Hz) | 80 | 237, 259 [M + Na] |

Step 6: Synthesis of Compound A7

To a solution of 166 g (0.63 mol) of compound A6 in THF/water (4/1, 1.66 L) are added 50.5 g (1.26 mol) of NaOH pellets in portions over 20 min. The reaction is stirred at room temperature for 2.5 d. The organic solvent is removed under reduced pressure and the aqueous residue is diluted with water (2 L) and washed with DCM (2 L). The aqueous layer is acidified to pH 1-2 with concentrated HCl and then extracted with DCM (3×2 L). The acidic aqueous is further saturated with NaCl and extracted again with DCM (6×2 L). The combined organic extracts are concentrated under reduced pressure to give 123 g of compound A7 as a white solid. Yield: 83%, ES-MS: m/z 235 [M−H]

According to this procedure the following compounds are synthesized

TABLE V

| Structure | $^1$H NMR | Yield [%] | m/z [M − H] |
|---|---|---|---|
| 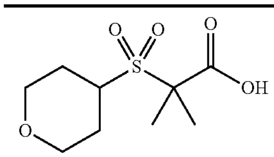 | (500 MHz, CHLOROFORM-d) δ ppm 1.71 (6 H, s), 1.94-2.12 (4 H, m), 3.47 (2 H, td, J = 11.41, 2.98 Hz), 3.73-3.86 (1 H, m), 4.07-4.15 (2 H, m), 6.82 (1 H, br. s.) | 69 | 235 |
| 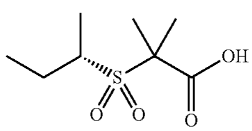 | (500 MHz, CHLOROFORM-d) δ ppm 1.06 (3 H, t, J = 7.48 Hz), 1.42 (3 H, d, J = 7.02 Hz), 1.59-1.75 (7 H, m), 1.98-2.15 (1 H, m), 3.43-3.58 (1 H, m), 6.09 (1 H, br. s.) | 40* | 207 |

*lithium hydroxide monohydrate is used instead of NaOH pellets.

Alternative Acid Method A:
Synthesis of Compound A7

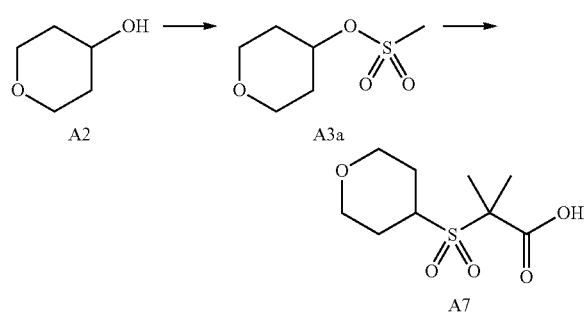

Step 1: Synthesis of Compound A3a 10 kg of compound A2 are dissolved in a mixture of 50 L toluene and 10.4 kg triethylamine. 11.55 kg methane sulfonyl chloride in 100 ml toluene are added while maintaining the internal temperature below 20° C. by cooling, and the addition funnel is rinsed with 50 ml toluene. The stirring is continued for one hour. The precipitate is filtered and the filter cake is washed twice with 20 L toluene each. The filtrate is concentrated by vacuum evaporation (60 L were distilled of), seeding crystals and 50 L methylcyclohexane are added. The suspension is cooled to 2° C. After 1 h the product is isolated by filtration, washed with 30 L methylcyclohexane and dried at 30° C. 16.6 kg of compound A3a are obtained as a white solid. Yield: 94%; $^1$H NMR (400 MHz, DMSO-d6) δ ppm 1.62-1.73 (2H, m), 1.92-2.00 (2H, m), 3.19 (3H, s), 3.42-3.49 (2H, m), 3.77-3.83 (2H, m), 4.80-4.88 (1H, m).

Step 2: Synthesis of Compound A7

30 g of compound A3a are dissolved in 270 ml degassed ethanol. 19.96 g potassium thioacetate are added and the reaction mixture is stirred at 77° C. for 12-18 h. Upon cooling to 20° C., the precipitate is filtered and rinsed twice with 90 ml degassed ethanol. 6.66 g sodium hydroxide solution (50%) are added to the filtrate, and the addition funnel is rinsed with 15 ml water. The reaction mixture is stirred at 25° C. for 1 h. 32.47 g 2-bromo-2-methyl-propionic acid ethyl ester ethyl are added to the mixture, and the addition funnel is rinsed with 30 ml ethanol. The stirring is continued for 1 h at 25° C. Afterwards, 450 ml solvent are removed by vacuum evaporation. 240 ml toluene are added and 120 ml solvent are distilled of. 90 ml water are added and the phases are separated. To the organic layer subsequently 90 ml water, 2.75 g sodium tungstate dihydrate and 2.83 g tetrabutylammonium hydrogen sulfate are added. The reaction mixture is heated to 85° C. and 80.88 g hydrogen peroxide solution (35%) are added over a period of 1 h. The addition funnel is rinsed with 30 ml water. The stifling is continued for 1 h at 85° C. The reaction mixture is filtered and the phases are separated. The organic phase is subsequently washed with 12.66 g sodium metabisulfite dissolved in 114 ml water and again with 126 ml water. 19.98 g sodium hydroxide solution (50%) are added to the organic layer and the addition funnel is rinsed with 45 ml water. The reaction mixture is warmed to 50° C. for 1 h. The phases are separated. The water phase is cooled to 5° C. and acidified with 27.07 g HCl (37%). The stirring at 5° C. is continued for 1 h. The precipitate is filtered, rinsed with 37.5 ml water and dried at 50° C. 14.03 g of compound A7 are obtained as a white solid. Yield: 35%. ES-MS: m/z 237 [M+H]; $^1$H NMR (400 MHz, DMSO-d6) δ ppm 1.53 (6H, s), 1.62-1.75 (2H, m), 1.85-1.92 (2H, m), 3.39 (2H, dt, $^3J_{H,H}$=2.1 Hz, $^3J_{H,H}$=11.7 Hz), 3.88-3.98 (3H, m), 13.63 (1H, s).

Acid Method B:
Synthesis of Compound B6

Step 2: Synthesis of compound B3

Prepared as described by adaptation of the following literature reference:

Radziszewski, J. G. et al. *J. Am. Chem. Soc.* 1993, 115, 8401.

To a solution of 97 g (810 mmol) of compound B2 in 2-methyltetrahydrofuran (190 mL) are added 165 mL of 50% aqueous NaOH solution. To this stirred suspension is added dropwise with cooling a solution of p-toluene-sulfonylchloride (283 g, 1.46 mol) in 2-methyltetrahydrofuran (280 mL). The reaction is stirred at 30-35° C. for 18 h. The suspension is poured into a mixture of ice-water (280 mL) and aqueous HCl solution (37%, 203 mL). After addition of methylcyclohexane (1.4 L) and further ice-water (0.2 L), the reaction mixture is stirred for 2 h in an ice-bath. The resulting crystalline precipitate is isolated by filtration and washed with methylcyclohexane (0.5 L) and water (0.5 L). Drying under reduced pressure at 40° C. gave 216 g of compound B3 as white crystalline solid. Yield: 99%, ES-MS: m/z 271 [M+H]; $^1$H NMR (400 MHz, CHLOROFORM-d) δ ppm 1.19-1.35 (2H, m), 1.54-1.63 (2H, m), 1.85-2.02 (1H, m), 2.45 (3H, s), 3.28-3.39 (2H, m), 3.86 (2H, d, J=6.60 Hz), 3.93 (2H, dd, J=11.37, 4.52 Hz), 7.35 (2H, d, J=9.29 Hz), 7.78 (2H, d, J=8.31 Hz)

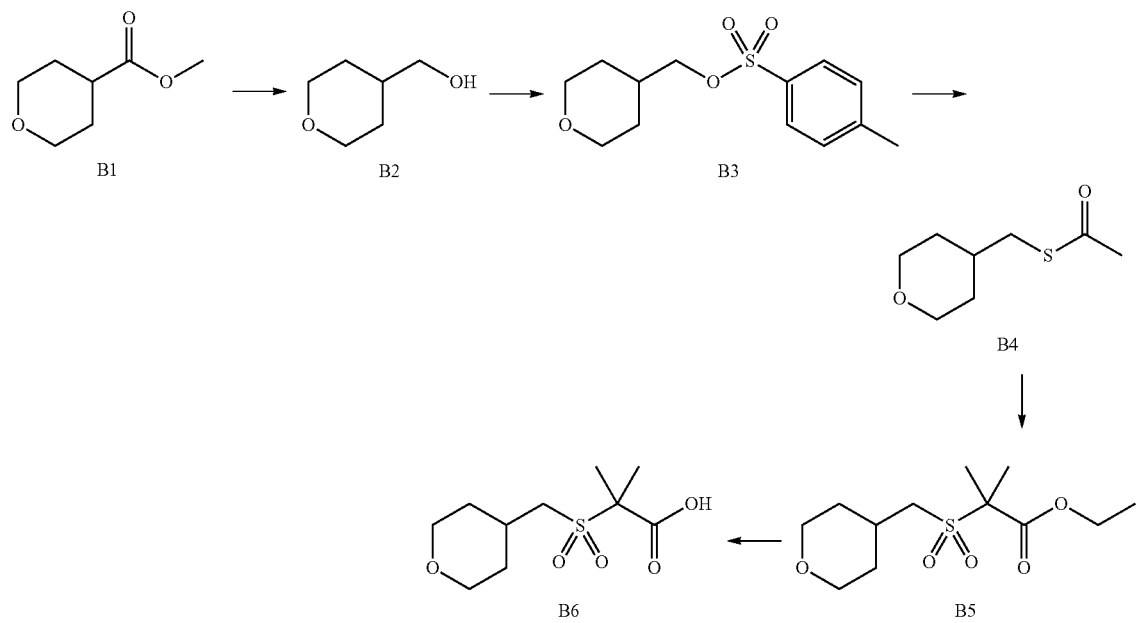

Step 1: Synthesis of Compound B2

To a solution of 250 mL of LiAlH$_4$ (2.3M solution in THF, 0.575 mol) in THF (200 mL) is added dropwise a solution of 130 mL (0.974 mol) of compound B1 in THF (900 mL) under nitrogen atmosphere (CAUTION: highly exothermic reaction!). The temperature is kept at 40-45° C. with an ice-bath. Upon complete addition, the reaction is stirred at room temperature for 1.5 h. The reaction is cooled in an ice-bath and quenched with addition of water (22 mL), 15% aqueous NaOH solution (21 mL) and water (66 mL). The resulting precipitate is removed by filtration through Celite® and is rinsed with THF (300 mL). The filtrate is concentrated under reduced pressure to afford 102.5 g of compound B2 as a clear oil. Yield: 91%; $^1$H-NMR (400 MHz, CHLOROFORM-d) δ ppm 1.20-1.39 (2H, m), 1.56-1.83 (3H, m), 2.03 (1H, br. s.), 3.29-3.52 (4H, m), 3.89-4.05 (2H, m)

Step 3: Synthesis of Compound B4

Prepared as described by adaptation of the following literature reference:

Watson, R. J. et al. *Tetrahedron Lett.* 2002, 43, 683-685.

To a solution of 224 g (0.83 mol) of compound B3 in methyl isobutylketone (1.6 L) are added 189 g (1.66 mol) of potassium thioacetate. The beige suspension is stirred at 70° C. for 4.5 h. The reaction mixture is cooled to room temperature and water (1.8 L) is added. The organic layer is washed with 10% aqueous K$_2$CO$_3$ solution (1.8 L) and water (1 L). The organic layer is filtered through Celite® (20 g), activated charcoal (20 g) and Na$_2$SO$_4$ (20 g) and the filtrate is concentrated under reduced pressure. The residual oil is azeotroped with methylcyclohexane (200 mL) and n-heptanes (250 mL) to afford 138 g of compound B4 as a yellow-orange oil (CAUTION: Stench!). Yield: 96%; ES-MS: m/z 175 [M+H]; $^1$H NMR (400 MHz, CHLOROFORM-d) δ ppm 1.23-1.40

(2H, m), 1.59-1.78 (3H, m), 2.33 (3H, d, J=4.16 Hz), 2.82 (2H, dd, J=6.24, 3.79 Hz), 3.27-3.39 (2H, m), 3.88-4.02 (2H, m)

Step 4: Synthesis of Compound B5

A solution of 90 g (516 mmol) of compound B4 in toluene (500 mL) under nitrogen atmosphere is cooled in an ice-bath. A solution of sodium ethoxide in ethanol (21%, 231 mL) is added and the reaction is stirred for 50 min. Then 76 mL (516 mmol) of ethyl α-bromoisobutyrate are added and the reaction stirred for 1 h. To the reaction mixture are added glacial acetic acid (8.9 mL) and water (500 mL). The organic layer is separated and washed with water (500 mL). A 3-neck round bottom flask is charged with water (500 mL), Oxone® (477 g, 775 mmol) and tetrabutylammonium-hydrogensulfate (5 g, 15 mmol) and the organic layer is added. The biphasic reaction mixture is stirred for 2 d at room temperature. The solids are removed by filtration and the layers of the filtrate are separated. The organic layer is washed with water (2×500 mL). The solvent is removed under reduced pressure and further azeotroped with toluene to give 125 g of compound B5. Yield: 87%; ES-MS: m/z 279 [M+H]; $^1$H NMR (250 MHz, CHLOROFORM-d) δ ppm 1.32 (3H, t, J=7.16 Hz), 1.39-1.59 (2H, m), 1.64 (6H, s), 1.81-1.97 (2H, m), 2.29-2.53 (1H, m), 3.15 (2H, d, J=6.55 Hz), 3.45 (2H, dd, J=1.83, 0.30 Hz), 3.88-4.03 (2H, m), 4.26 (2H, d, J=7.16 Hz)

Step 5: Synthesis of Compound B6

To a solution of 123 g (0.44 mol) of compound B5 in THF (450 mL) are added 663 mL of 2M aqueous sodium hydroxide solution (1.33 mol). The reaction is stirred at room temperature for 1 h. To the reaction mixture is added TBME (1.25 L) and the layers are separated. The aqueous layer is cooled in an ice bath and then acidified with 37% aqueous HCl solution (123 mL). The resulting precipitate is isolated by filtration, washed with water (200 mL) and dried under reduced pressure at 50° C. to afford 101 g of compound B6 as white crystalline solids. Yield: 91%; ES-MS: m/z 251 [M+H]; $^1$H NMR (400 MHz, DMSO-d6) δ ppm 1.31-1.45 (2H, m), 1.49 (6H, s), 1.70-1.79 (2 H, m), 2.13-2.28 (1H, m), 3.24 (2H, d, J=6.60 Hz), 3.28-3.38 (2H, m), 3.76-3.85 (2H, m), 13.65 (1H, br. s.)

Acid Method C:
Synthesis of Compound C5 extracted with ethyl acetate (3×500 mL). The organic fractions are combined, washed with brine (300 mL), dried over MgSO$_4$, filtered and concentrated under reduced pressure. Purification by chromatography on silica eluting with heptanes/dichloromethane provides 44 g of compound C2. Yield: 73%; m/z 191 [M+H]; $^1$H NMR (250 MHz, CHLOROFORM-d) δ ppm 1.18-1.30 (3H, m), 1.57 (6H, s), 2.27 (3H, s), 4.19 (2H, q, J=7.16 Hz)

Step 2: Synthesis of Compound C3

To a solution of 149 g (0.785 mol) of compound C2 in ethanol (1.2 L, degassed under nitrogen for 1 h) are added 169.7 g (0.105 mol) of sodium methoxide, followed by a solution of 150 g (0.785 mol) of 4-bromo-1,1,1-trifluorobutane. The reaction is heated to 85° C. for 3 d. The solvent is removed under reduced pressure. The residue is dissolved in DCM (1 L) and washed with saturated aqueous NaHCO$_3$ solution (2×1 L). The organic layer is dried over Na$_2$SO$_4$, filtered and the filtrate is concentrated under reduced pressure to afford 171 g of compound C3 as a brown oil. Yield: 84%; ES-MS: m/z 259 [M+H]; $^1$H NMR (500 MHz, CHLOROFORM-d) δ ppm 1.29 (3H, t, J=7.17 Hz), 1.51 (6H, s), 1.76-1.86 (2H, m), 2.12-2.27 (2H, m), 2.69 (2H, t, J=7.17 Hz), 4.18 (2H, q, J=7.17 Hz)

Step 3: Synthesis of Compound C4

To a solution of 220 g (0.852 mol) of compound C3 in dioxane/water (1/1, 4 L) are added 1047 g (1.703 mol) of Oxone® in portions over 0.5 h at room temperature. The reaction mixture is stirred at room temperature for 18 h. The solid is removed by filtration and rinsed with dioxane (0.5 L). The filtrate is concentrated under reduced pressure to remove the organic solvent. The aqueous residue is extracted with DCM (2×1 L). The combined organic extracts are washed with saturated aqueous NaHCO$_3$ solution (2 L), dried over Na$_2$SO$_4$ and filtered. The filtrate is concentrated under reduced pressure to afford 226 g of compound C4 as dark yellow oil. Yield 92%; ES-MS: m/z 291 [M+H]; $^1$H NMR (500 MHz, CHLOROFORM-d) δ ppm 1.32 (3H, t, J=7.17 Hz), 1.66 (6H, s), 2.20 (2H, quin, J=7.59 Hz), 2.28-2.41 (2H, m), 3.34 (2H, t, J=7.48 Hz), 4.27 (2H, q, J=7.17 Hz)

Step 4: Synthesis of Compound C5

To a solution of 170 g (0.59 mol) of compound C4 in THF (3.4 L) are added 225.4 g (1.76 mol) of potassium trimethyl-

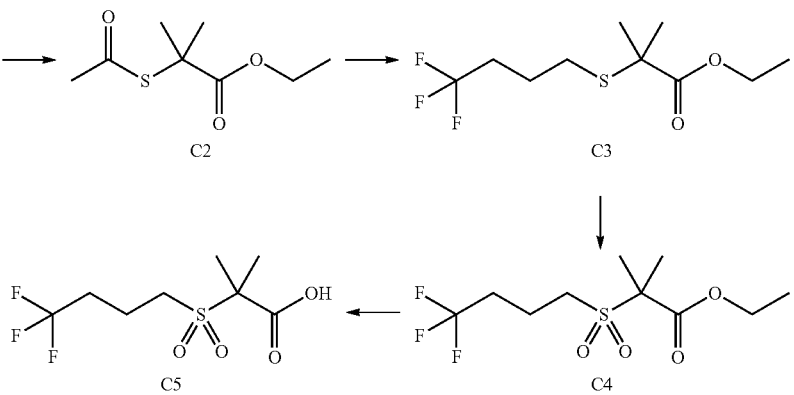

Step 1: Synthesis of Compound C2

To a solution of compound C1 (62 g, 0.32 mol) in DMF (500 mL) at room temperature is added potassium thioacetate (72 g, 0.63 mol). The reaction is stirred for 16 h and then concentrated under reduced pressure. The residue is diluted with a 2M aqueous hydrochloric acid solution (500 mL) and silanolate in portions over 0.5 h. The reaction is stirred at room temperature for 18 h. The reaction mixture is acidified with 2M aqueous HCl solution (2 L) to pH 2 and extracted with DCM (2×2 L). The combined organic extracts are dried (Na$_2$SO$_4$) and filtered. The filtrate is concentrated under reduced pressure to afford 143 g of compound C5 as yellow solids. Yield: 93%; ES-MS: m/z 261 [M−H]. $^1$H-NMR (500 MHz, CHLOROFORM-d) δ ppm 1.71 (6H, s), 2.18-2.28 (2H, m), 2.30-2.42 (2H, m), 3.38 (2H, t, J=7.48 Hz), 6.96 (1H, br. s.)

Acid Method D:
Synthesis of Compound D6

(20 mL) and extracted with ethyl acetate (3×50 mL). The combined organic extracts are dried over Na$_2$SO$_4$, filtered and the solvent is removed to give 1.9 g of compound D3 as off-white crystalline solid. Yield: 53%; ES-MS: m/z 285 [M+H]; $^1$H-NMR (500 MHz, CHLOROFORM-d) δ ppm 1.17-1.29 (2H, m), 1.45-1.52 (2H, m), 1.57-1.67 (3H, m),

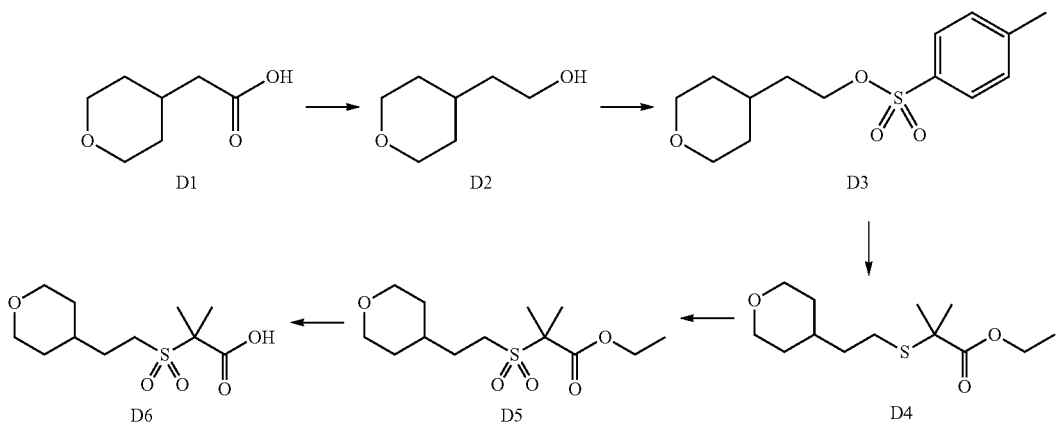

Step 1: Synthesis of Compound D2

To a suspension of 0.55 g of LiAlH$_4$ (13.9 mmol) in THF (10 mL) is added dropwise a solution of 2 g (13.9 mmol) of compound D1 in THF (10 mL) under nitrogen atmosphere (CAUTION: highly exothermic reaction!). Upon complete addition, the reaction is stirred at room temperature for 18 h. The reaction is cooled in an ice-bath and quenched with addition of 1M aqueous NH$_4$Cl solution (2 mL). The resulting precipitate is removed by filtration through Celite® and is rinsed with ethyl acetate (3×100 mL). The filtrate is dried over Na$_2$SO$_4$, filtered and concentrated under reduced pressure to afford 1.63 g of compound D2 as a colorless oil. Yield: 90%; ES-MS m/z 131 [M+H]; $^1$H-NMR (500 MHz, CHLOROFORM-d) δ ppm 1.29 (2H, qd, J=12.08, 4.04 Hz), 1.50 (2H, qd, J=6.71, 1.37 Hz), 1.55-1.73 (3H, m), 1.95-2.07 (1H, m), 3.37 (2H, t, J=11.83 Hz), 3.66 (2H, t, J=6.03 Hz), 3.92 (2H, dd, J=11.44, 4.12 Hz)

Step 2: Synthesis of Compound D3

To a solution of 1.63 g (12.5 mmol) of compound D2 in pyridine (15 mL) are added 3.58 g (18.8 mmol) of p-toluenesulfonylchloride. The reaction is stirred at room temperature for 5 h. The reaction mixture is concentrated under reduced pressure. The residue is dissolved 2M aqueous HCl solution 2.46 (3H, s), 3.32 (2H, td, J=11.78, 1.93 Hz), 3.91 (2H, dd, J=11.28, 4.13 Hz), 4.08 (2H, t, J=6.14 Hz), 7.36 (2H, d, J=8.07 Hz), 7.80 (2H, d, J=8.44 Hz)

Step 3: Synthesis of Compound D4

To a solution of 1.9 g (6.7 mmol) of compound D3 in ethanol (20 mL) are added 1.4 g (26.8 mmol) of sodium methoxide, followed by 1.27 g (6.7 mmol) of 2-acetylsulfanyl-2-methyl-propionic acid ethyl ester. The reaction mixture is heated in a microwave at 130° C. for 0.5 h. The solvent is removed under reduced pressure. The residue is partitioned between saturated aqueous NaHCO$_3$ solution (25 mL) and DCM (25 mL). The layers are separated and the aqueous phase extracted with DCM (2×25 mL). The combined organic extracts are dried over Na$_2$SO$_4$, filtered and the solvent is removed under reduced pressure to afford 1.9 g of compound D4. Yield: 100%; ES-MS: m/z 261 [M+H]; $^1$H NMR (250 MHz, CHLOROFORM-d) δ ppm 1.15-1.38 (5H, m), 1.42-1.70 (12H, m), 2.59-2.71 (1H, m), 3.37 (2H, td, J=11.73, 1.98 Hz), 3.95 (2H, ddd, J=11.04, 3.88, 0.91 Hz), 4.18 (2H, q, J=7.16 Hz)

According to this procedure the following compound are synthesized:

TABLE VI

| Structure | $^1$H NMR | Yield [%] | m/z [M + H] |
|---|---|---|---|
| (structure shown) | (250 MHz, CHLOROFORM-d) δ ppm 1.15-1.38 (5 H, m), 1.42-1.70 (12 H, m), 2.59-2.71 (1 H, m), 3.37 (2 H, td, J = 11.73, 1.98 Hz), 3.95 (2 H, ddd, J = 11.04, 3.88, 0.91 Hz), 4.18 (2 H, q, J = 7.16 Hz) | 100 | 261 |
| (structure shown) | (400 MHz, CHLOROFORM-d) δ ppm 1.20 (t, 3H), 1.43 (s, 6H), 1.52-1.64 (m, 8H), 2.91-2.93 (m, 1H), 3.18 (s, 3H), 3.20-3.23 (m, 1H), 4.08 (q, 2H) | 33[a] | N/A |

[a]Reaction performed in a sealed tube at 120° C. in an oil bath.

Step 4: Synthesis of Compound D5

A 3-neck roundbottom flask is charged with 1.9 g (7.3 mmol) of compound D4 and dissolved in 1,4-dioxane/water (4/1, 40 mL). Oxone® (9 g, 14.6 mmol) is added in one portion. The biphasic reaction mixture is stirred at room temperature for 2 h. The solids are removed by filtration and the filtrate is concentrated under reduced pressure. The residue is washed with saturated aqueous $NaHCO_3$ solution (50 mL) and extracted with DCM (3×50 mL). The combined organic layers are dried over $Na_2SO_4$, filtered and the solvent is removed under reduced pressure to give 1.34 g of compound D5. Yield: 63%; ES-MS: m/z 293 [M+H], 315 [M+Na]; $^1$H NMR (250 MHz, CHLOROFORM-d) δ ppm 1.28-1.45 (5H, m), 1.59-1.71 (9H, m), 1.79-1.95 (2H, m), 3.20-3.31 (2H, m), 3.38 (2H, td, J=11.76, 1.90 Hz), 3.93-4.04 (2H, m), 4.27 (2H, q, J=7.06 Hz)

According to this procedure the following compound are synthesized:

TABLE VII

| Structure | $^1$H NMR | Yield [%] | m/z [M + H] |
| --- | --- | --- | --- |
| 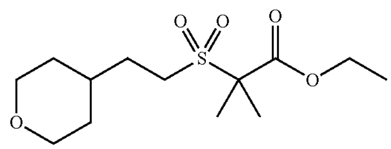 | (250 MHz, CHLOROFORM-d) δ ppm 1.28-1.45 (5 H, m), 1.59-1.71 (9 H, m), 1.79-1.95 (2 H, m), 3.20-3.31 (2 H, m), 3.38 (2 H, td, J = 11.76, 1.90 Hz), 3.93-4.04 (2 H, m), 4.27 (2 H, q, J = 7.06 Hz) | 63 | 293 |
| 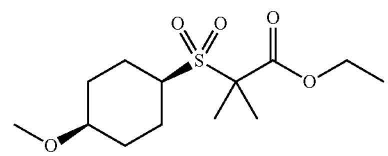 | (400 MHz, CHLOROFORM-d) δ ppm 1.32 (3H, t, 7.2 Hz), 1.42-1.49 (2H, m), 1.65 (6H, s), 1.86-2.10 (6H, m), 3.28 (3H, s), 3.43 (1H, m), 3.52-3.56 (1H, m), 4.18 (2H, q, 7.2 Hz) | 93 | 293 |

Step 5: Synthesis of Compound D6

To a solution of 1.34 g (4.6 mmol) of compound D5 in THF (40 mL) are added 1.17 g (9.2 mmol) of potassium trimethylsilanolate. The reaction is stirred at room temperature for 2 h. The solvent is removed under reduced pressure. The residue is partitioned between DCM (50 mL) and 1M aqueous HCl solution (10 mL). The aqueous layer is extracted with DCM (2×50 mL). The combined organic extracts are dried over $Na_2SO_4$, filtered and the filtrate is concentrated under reduced pressure to afford 1.02 g of compound D6. Yield: 84%, ES-MS: m/z 263 [M−H]; $^1$H NMR (500 MHz, MeOD) δ ppm 1.29 (2H, dt, J=12.17, 2.08 Hz), 1.56-1.85 (11H, m), 3.35-3.45 (4H, m), 3.88-3.97 (2H, m)

According to this procedure the following compounds are synthesized

TABLE VIII

| Structure | $^1$H NMR | Yield [%] | m/z [M − H] |
| --- | --- | --- | --- |
| 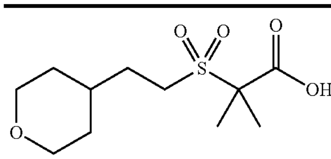 | (500 MHz, MeOD) δ ppm 1.29 (2 H, dt, J = 12.17, 2.08 Hz), 1.56-1.85 (11 H, m), 3.35-3.45 (4 H, m), 3.88-3.97 (2 H, m) | 84 | 263 |
| 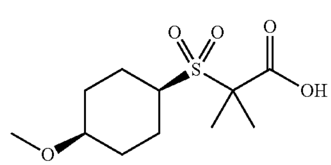 | (500 MHz, CHLOROFORM-d) δ ppm 1.40-1.50 (2 H, m), 1.71 (6 H, s), 1.86-1.94 (2 H, m), 1.98-2.08 (2 H, m), 2.09-2.16 (2 H, m), 3.31 (3 H, s), 3.37-3.45 (1 H, m), 3.47 (1 H, quin, J = 2.94 Hz) | 90 | 263 |

Acid Method E:

Synthesis of Compound E4

Prepared as described by adaptation of the following reference: WO2008014199, Boehringer Ingelheim.

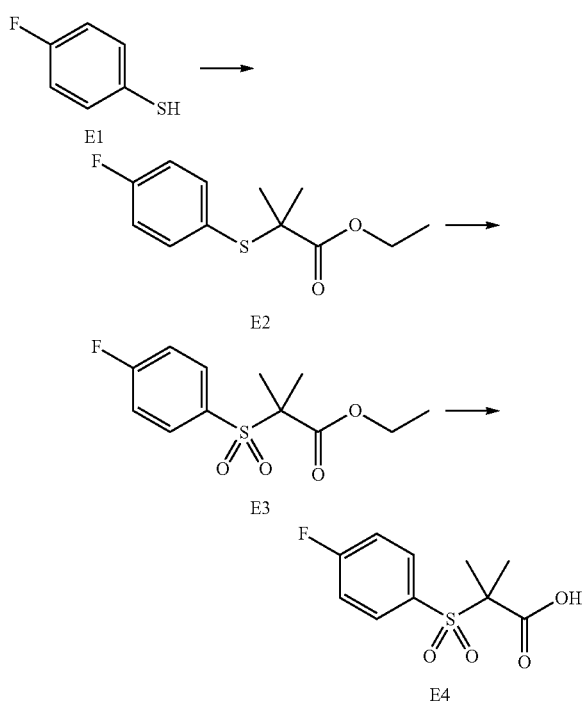

294 g (479 mmol) of Oxone®. The white suspension is stirred at room temperature for 17 h. The white solid is separated by filtration and washed with 1,4-dioxane (200 mL). The filtrate is concentrated under reduced pressure to remove the organic solvent. The resulting aqueous solution is extracted with DCM (3×1 L). The combined organic extracts are washed with saturated aqueous NaHCO$_3$ solution (500 mL), brine, dried over Na$_2$SO$_4$ and filtered. The filtrate is concentrated under reduced pressure to afford 70 g of compound E3 as yellow oil. Yield: 87%, ES-MS: m/z 275 [M+H]; $^1$H-NMR (400 MHz, CHLOROFORM-d) δ ppm 1.15 (3H, t, J=7.09 Hz), 1.55 (6H, s), 4.08 (2H, q, J=7.17 Hz), 7.13-7.22 (2H, m), 7.78-7.86 (2H, m)

Step 3: Synthesis of Compound E4

To a solution of 70 g (255 mmol) of compound E3 in THF/water (6/1, 700 mL) are added 21.4 g (510 mmol) of lithium hydroxide monohydrate. The reaction is stirred at room temperature for 18 h. The reaction is acidified with 2M aqueous HCl solution (500 mL) to pH 1. The acidic aqueous layer is extracted with DCM (3×1000 mL). The combined organic extracts are dried over Na$_2$SO$_4$ and filtered. Concentration of the filtrate under reduced pressure affords 60.5 g of compound E4. Yield: 96%, ES-MS: m/z 247, 264 [M+H$_2$O]; $^1$H-NMR (500 MHz, MeOD) δ ppm 1.57 (6H, s), 7.35 (2H, t, J=8.85 Hz), 7.94 (2H, dd, J=9.00, 5.04 Hz)

Acid Method F:

Synthesis of Synthesis of Compound F5

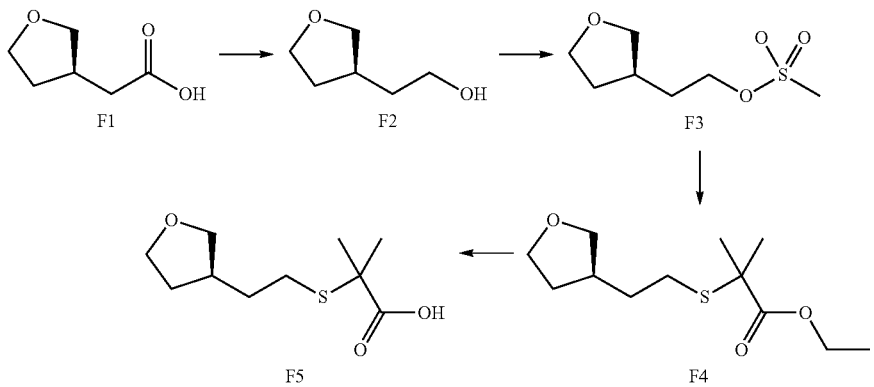

Step 1: Synthesis of Compound E1

To a solution of 50 g (390 mmol) of compound E1 in ethanol (400 mL) are added 21.9 g (390 mmol) of KOH pellets, followed by 57 mL (390 mmol) of ethyl α-bromoisobutyrate. The reaction is heated to reflux for 2 h and then cooled to room temperature. The solid (KBr) is separated by filtration and rinsed with ethanol (20 mL). The filtrate is concentrated under reduced pressure and the residue dissolved in DCM (500 mL). The organic layer is washed with saturated aqueous NaHCO$_3$ solution (250 mL). The aqueous washes are back-extracted with DCM (2×500 mL). The combined organics are washed with brine, dried over Na$_2$SO$_4$. Filtration and concentration under reduced pressure affords 74.9 g of compound E2 as yellow oil. Yield: 79%, ES-MS: m/z 243 [M+H]; $^1$H-NMR: (400 MHz, CHLOROFORM-d) δ ppm 1.22 (3H, t, J=7.09 Hz), 1.47 (6H, s), 4.11 (2H, q, J=7.25 Hz), 7.01 (2H, t, J=8.68 Hz), 7.39-7.50 (2H, m)

Step 2: Synthesis of Compound E3

To a solution of 71 g (293 mmol) of compound E2 in 1,4-dioxane/water (6/1, 700 mL) are added in several portions Step 1: Synthesis of Compound F2

To a solution of 3.90 g (30 mmol) of compound F1 (prepared as described in Ghosh, A. K. et al. *J. Med. Chem.* 1993, 36, 2300-2310) in anhydrous THF (30 ml) is added 3.03 ml of borane (48 mmol) slowly at 0° C. The reaction is warmed to room temperature and stirred for 6 h, then 3M aqueous NaOH solution (26 mL) is added and the mixture is stirred for 1 h. The pH is then adjusted to 11 with 6M aqueous HCl solution and the aqueous mixture is saturated with potassium carbonate. The basic aqueous solution is extracted with diethyl ether (3×100 mL). The combined organic extracts are dried (MgSO$_4$), filtered and the filtrate is concentrated under reduced pressure to give 2.54 g of compound F2. Yield: 73%; $^1$H NMR (500 MHz, CHLOROFORM-d) δ ppm 1.47-1.73 (3H, m), 1.98 (1H, br. s.), 2.02-2.12 (1H, m), 2.31 (1H, dt, J=14.80, 7.40 Hz), 3.37 (1H, t, J=7.78 Hz), 3.59-3.79 (3H, m), 3.85 (1H, td, J=8.32, 4.58 Hz), 3.91 (1H, t, J=7.78 Hz).

Step 2: Synthesis of Compound F3

To a solution of 1.86 g (16 mmol) of compound F2 in anhydrous THF (28 mL) are added triethyl amine (2.48 mL, 17.6 mmol) and methanesulfonyl chloride (1.36 mL, 17.6 mmol) slowly at 0° C. The reaction is stirred at room temperature for 2 h. The mixture is diluted with ethyl acetate (100 mL) and washed with saturated aqueous NaHCO₃ solution (2×50 mL) and 1M aqueous HCl solution (2×50 mL). The organic layer is dried (MgSO₄), filtered and the filtrate is concentrated under reduced pressure to afford 3.1 g of compound F3. Yield: 100%; $^1$H NMR (250 MHz, CHLOROFORM-d) δ ppm 1.48-1.62 (1H, m), 1.78-1.93 (1H, m), 2.01-2.20 (1H, m), 2.24-2.43 (1H, m), 3.02 (3H, s), 3.40 (1H, t, J=7.69 Hz), 3.73-3.99 (3H, m), 4.26 (2H, t, J=6.47 Hz)

Step 3: Synthesis of Compound F4

To a solution of 3.0 g (16 mmol) of compound C2 (prepared according to acid method C, step 1) in ethanol (50 mL, degassed) are added 3.45 g (54 mmol) of sodium methoxide, followed by 3.1 g (16 mmol) of compound F3 under nitrogen atmosphere. The reaction is heated to 80° C. for 16 h. The solvent is removed under reduced pressure. The residue is dissolved in ethyl acetate (50 mL) and washed with saturated aqueous NaHCO₃ solution (2×15 mL) and 1M aqueous HCl solution (2×15 mL). The organic layer is dried over Na₂SO₄, filtered and the filtrate is concentrated under reduced pressure. The residue is purified twice by column chromatography (silica, eluent: heptanes, ethyl acetate) to afford 0.43 g of compound F4. This intermediate (67% purity) is taken on to the next step. Yield: 29%; m/z 247 [M+H]

Step 4: Synthesis of Compound F5

To a solution of 1.68 g (6.82 mmol) of compound F4 in THF are added 6.82 mL (13.64 mmol) of 2M aqueous sodium hydroxide solution. The reaction is stirred at room temperature for 18 h. Then methanol (0.5 mL) and lithium hydroxide monohydrate (572 mg, 13.64 mmol) are added the reaction is heated to 45° C. for 16 h. Additional lithium hydroxide monohydrate (572 mg, 13.64 mmol) is added and the reaction is heated to 55° C. for 3 h. The reaction mixture is partitioned between DCM (8 mL) and water (10 mL). The aqueous layer is cooled in an ice bath, acidified with 6M aqueous HCl solution to pH 1 and extracted with DCM (3×15 mL). The combined organic extracts are dried (MgSO₄), filtered and the filtrate is concentrated under reduced pressure to afford 1.51 g of compound F5. Yield: 85%; m/z 219 [M+H]; $^1$H NMR (250 MHz, CHLOROFORM-d) δ ppm 1.43-1.73 (9H, m), 1.98-2.15 (1H, m), 2.31 (1H, quin, J=7.35 Hz), 2.58-2.74 (2H, m), 3.37 (1H, dd, J=8.30, 7.23 Hz), 3.68-3.99 (3H, m), 7.71 (1H, br. s.)

Acid Method G:
Synthesis of Compound G3

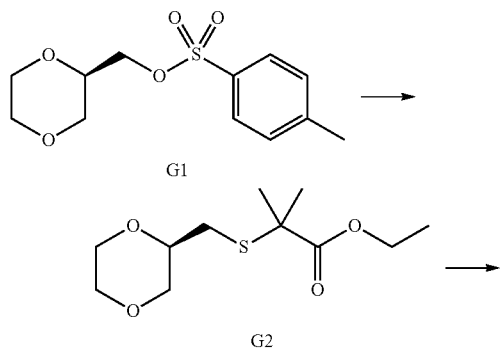

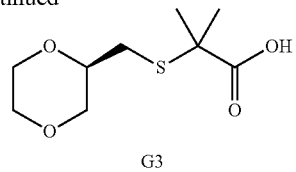

G3

Step 1: Synthesis of Compound G2

To a solution of 0.27 g (1.42 mmol) of compound C1 in ethanol (4 mL, degassed) are added 0.31 g (5.7 mmol) of sodium methoxide, followed by 0.39 g (1.42 mmol) of compound G1 (prepared according to WO2008/119663, F. Hoffmann-La Roche AG) under nitrogen atmosphere. The reaction is heated in a microwave to 130° C. for 0.5 h. The solvent is removed under reduced pressure. The residue is dissolved in DCM (10 mL) and washed with saturated aqueous NaHCO₃ solution (10 mL). The aqueous layer is extracted with DCM (10 mL). The combined organic extracts are dried over Na₂SO₄, filtered and the filtrate is concentrated under reduced pressure. The residue is purified by column chromatography (silica, eluent: heptanes, 20% ethyl acetate) to afford 0.17 g of compound G2 (UV purity: 77%). Yield: 61%; m/z 271 [M+Na]; $^1$H NMR (500 MHz, CHLOROFORM-d) δ ppm 1.29 (3H, t, J=7.17 Hz), 1.49-1.54 (6H, m), 2.59-2.66 (1H, m), 2.70-2.77 (1H, m), 3.28-3.36 (1H, m), 3.55-3.63 (1H, m), 3.64-3.76 (3H, m), 3.77-3.85 (2H, m), 4.18 (2H, q, J=7.17 Hz)

Step 2: Synthesis of Compound G3

To a solution of 169 mg (0.68 mmol) of compound G2 in THF/water (1/1, 10 mL) are added 102 mg (1.36 mmol) of lithium hydroxide monohydrate. The reaction is stirred at room temperature for 18 h. Then additional THF/water (1/1, 10 mL) is added and the reaction is for further 48 h. The reaction mixture is concentrated under reduced pressure. The aqueous residue is washed with diethyl ether (10 mL), then acidified with 6M aqueous HCl solution and extracted with ethyl acetate (3×10 mL). The combined organic extracts are dried (MgSO₄), filtered and the filtrate is concentrated under reduced pressure to afford 147 mg of compound G3. Yield: 86%; ES-MS: m/z 243 [M+Na]; $^1$H NMR (500 MHz, CHLOROFORM-d) δ ppm 1.55 (6H, s), 2.65-2.72 (1H, m), 2.73-2.81 (1H, m), 3.32-3.41 (1H, m), 3.57-3.64 (1H, m), 3.68-3.77 (3H, m), 3.77-3.86 (2H, m)

Amine Method a:
Synthesis of Compound a3

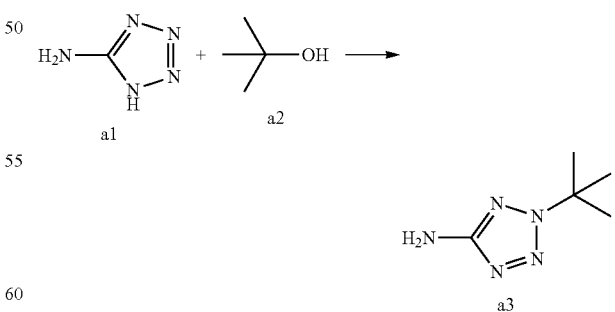

The synthesis of compound a 3 is by adaptation of the following literature procedure: Henry, R. A. *J. Heterocyclic Chem.* 1976, 13, 391.

To a stirred solution of 28.7 g (388 mmol) of compound a2 and 72.7 g (353 mmol) of dicyclohexyl carbodiimide in DCM (300 mL) are added 0.411 g of CuCl$_2$ at room temperature. The reactions mixture is stirred for 96 h, then 30 g (353 mmol) of compound a1 in DCM are added and the reaction is stirred at room temperature for 48 h. The reaction mixture is filtered and the solid is washed with DCM. The organic filtrate is washed with water and brine and dried over Na$_2$SO$_4$. Filtration and concentration of the filtrate under reduced pressure. The residue is purified by column chromatography (silica, eluent DCM, 5% methanol) to afford 6 g of compound a3 as an off-white powder. Yield 12%; ES-MS: m/z 142 [M+H]; mp 114-119° C. (lit. 116-117° C.); $^1$H NMR (250 MHz, CHLOROFORM-d) δ ppm 1.68 (9H, s), 3.91 (2H, br. s.)

Amide Method A:

Synthesis of Example 1:

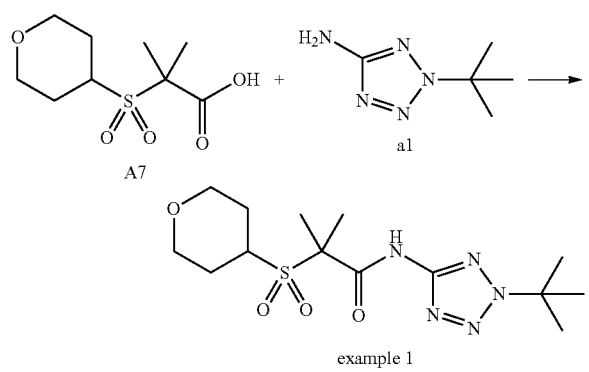

example 1

Activation of 150 mg (0.68 mmol) of compound A7 as the corresponding acid chloride is achieved by treatment with thionyl chloride (2 mL) at 50° C. for 2 h. The reaction is cooled to room temperature and excess thionyl chloride is removed under reduced pressure. Compound a1 (113 mgs, 0.8 mmols) and N,N-diisopropylethylamine (348 µL, 2.0 mmol) is dissolved in anhydrous tetrahydrofuran (2 mL). The crude acid chloride (102 mg, 0.4 mmol) is dissolved in tetrahydrofuran (1 mL) and is added to the amine solution. The reaction is placed on an orbital shaker for 16 hours at 50° C. The reaction is cooled to room temperature and is concentrated. The crude product is dissolved in 10% H$_2$O/DMSO (2 mL). Purification by preparative HPLC provides example 1 (31 mg, 0.087 mmol). Yield: 13%; ES-MS: m/z 360.1 [M+H], retention time (LC method a): 0.70 min Compounds in Table X, amide method A, are made according to this procedure.

Amide Method B:

Synthesis of Example 5:

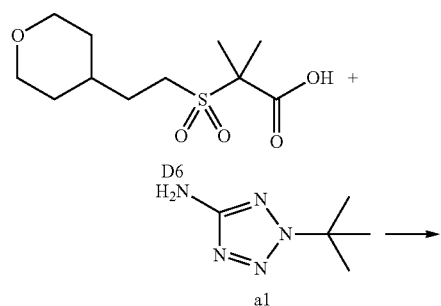

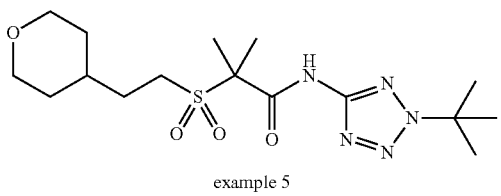

example 5

Activation of 421 mg (1.59 mmol) of compound D6 as the corresponding acid chloride is achieved by treatment with thionyl chloride (3 mL) at 50° C. for 3 h. The reaction is cooled to room temperature and excess thionyl chloride is removed under reduced pressure.

The crude acid chloride is dissolved in anhydrous THF (5 mL) and N,N-diisopropylethylamine (0.37 mL, 2.1 mmol) is added, followed by compound a1 (150 mgs, 1.06 mmols). The reaction is stirred at 70° C. for 3 h. The reaction is cooled to room temperature and is concentrated under reduced pressure. The residue is dissolved in DCM (10 mL) and washed with saturated aqueous NaHCO$_3$ solution (10 mL). The aqueous layer is back-extracted with DCM (5 mL). The combined organic extracts are dried (Na$_2$SO$_4$), filtered and the filtrate is concentrated under reduced pressure. The crude product is purified by column chromatography (silica, eluent: heptanes: 0-50% ethyl acetate) to afford 239 mg of example 5. Yield: 58%; ES-MS: m/z 388.2 [M+H]; retention time (LC method b): 3.67 min; $^1$H NMR (500 MHz, CHLOROFORM-d) δ ppm 1.20-1.41 (2H, m), 1.57-1.65 (3H, m), 1.76 (9H, s), 1.78 (6H, s), 1.82-1.94 (2H, m), 3.02-3.18 (2H, m), 3.25-3.46 (2H, m), 3.86-4.04 (2H, m), 9.30 (1H, s)

Compounds in Table X, amide method B, are made according to this procedure with the following modifications to be noted: for example 2, acid chloride formation is achieved using thionyl chloride in toluene at 100° C. for 2 h and for the amide formation toluene is also used instead of THF. For example 3 and 4 acid chloride formation is achieved using thionyl chloride (2 eq.), DMF (cat.) in toluene at 50° C. for 3 h and for the amide formation toluene is also used instead of THF. Example 6 is purified twice by column chromatography (silica, eluent: heptanes, 0-50% ethyl acetate), followed by mass-directed preparative LCMS (neutral method). For example 8-9, acid chloride formation is achieved using oxalyl chloride (2 eq.), DMF (cat.) in DCM at room temperature for 18 h.

Amide Method C:

Synthesis of Example 7:

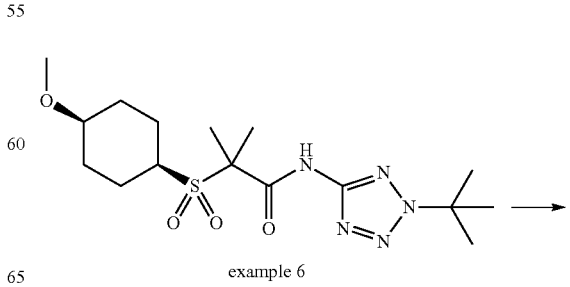

example 6

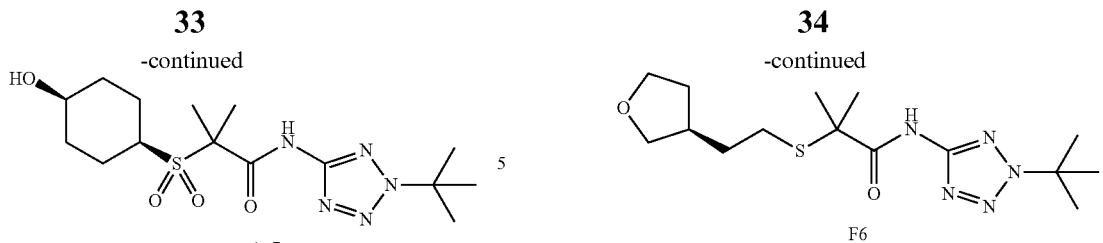

example 7

To a solution of 206 mg (0.77 mmol) of aluminium tribromide in ethanethiol (2.5 mL) is added a solution of 100 mg (0.26 mmol) of example 6 in ethanethiol (2.5 mL). The reaction is stirred at room temperature for 3 h. The reaction is quenched by addition of 6M aqueous HCl solution (3 mL) and diluted with water (10 mL). The layers are separated and the aqueous layer is extracted with DCM (3×20 mL). The combined organic extracts are dried over $Na_2SO_4$, filtered and the filtrate is concentrated under reduced pressure. The residual solid is purified by column chromatography (silica, eluent: heptanes, 0-50% ethyl acetate) to afford 70 mg of example 7. Yield: 73%, ES-MS: m/z 374.3 [M+H]; retention time (LC method b): 3.30 min; $^1$H NMR (500 MHz, CHLOROFORM-d) δ ppm 1.45-1.66 (3H, m), 1.69-1.82 (15H, m), 1.84-1.99 (4H, m), 2.03-2.22 (2H, m), 3.16-3.38 (1H, m), 4.05 (1H, d, J=2.59 Hz), 9.62 (1H, s)

Compounds in Table X, amide method C, are made according to this procedure.

Amide Method D:

Synthesis of Example 10:

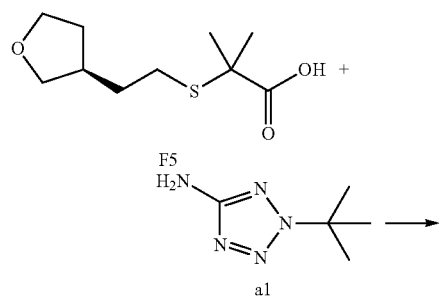

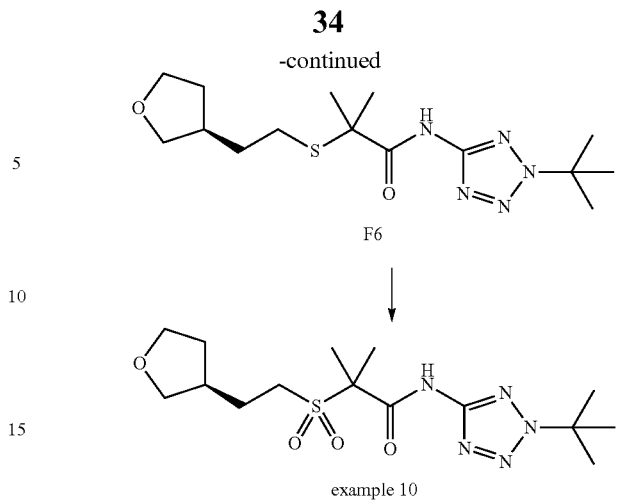

example 10

Step 1: Synthesis of Compound F6

Activation of 92 mg (0.42 mmol) of compound F5 as the corresponding acid chloride is achieved by treatment with oxalyl chloride (0.07 mL, 0.84 mmol) and DMF (cat., 1 drop) in DCM (3 mL) at room temperature for 3 h. The reaction mixture is concentrated under reduced pressure. The residue is dissolved in anhydrous THF (2 mL) and concentrated under reduced pressure. This process is repeated.

Then the crude acid chloride is dissolved in anhydrous THF (3 mL) and 0.22 mL (1.26 mmol) of N,N-diisopropylethylamine are added followed by 59 mg (0.42 mmol) of compound a1. After complete addition the reaction is heated to 60° C. for 17 h. The reaction is cooled to room temperature and the solvent is removed under reduced pressure. The residue is dissolved in ethyl acetate (20 mL) and washed with saturated aqueous $NaHCO_3$ solution (2×5 mL) and 1M aqueous HCl solution (2×5 mL). The organic layer is dried ($Na_2SO_4$) and filtered. The filtrate is concentrated under reduced pressure and the residue purified by column chromatography (silica, eluent heptanes, 0-20% ethyl acetate) to yield 64 mg of compound F6. Yield: 44%; ES-MS: m/z 342 [M+H], retention time (LC method c): 1.91 min; $^1$H NMR (250 MHz, CHLOROFORM-d) δ ppm 1.39-1.57 (1H, m), 1.58-1.73 (8H, m), 1.76 (9H, s), 1.94-2.11 (1H, m), 2.20-2.37 (1H, m), 2.58 (2H, td, J=7.61, 2.89 Hz), 3.32 (1H, dd, J=8.38, 7.01 Hz), 3.64-3.93 (3H, m), 9.44 (1H, s).

According to the above method the following compounds are synthesized

TABLE IX

| Structure | $^1$H NMR | Yield [%] | m/z [M + H] |
|---|---|---|---|
| 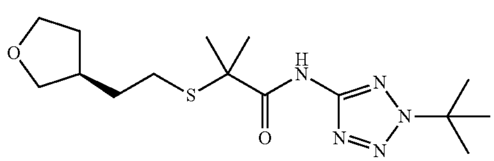 | (250 MHz, CHLOROFORM-d) δ ppm 1.39-1.57 (1 H, m), 1.58-1.73 (8 H, m), 1.76 (9 H, s), 1.94-2.11 (1 H, m), 2.20-2.37 (1 H, m), 2.58 (2 H, td, J = 7.61, 2.89 Hz), 3.32 (1 H, dd, J = 8.38, 7.01 Hz), 3.64-3.93 (3 H, m), 9.44 (1 H, s). | 44 | 342 |
| 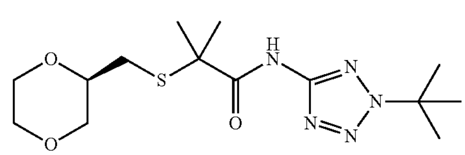 | (500 MHz, CHLOROFORM-d) δ ppm 1.63 (3 H, s), 1.63 (3 H, s), 1.76 (9 H, s), 2.61-2.64 (2 H, m), 3.29-3.36 (1 H, m), 3.53-3.60 (1 H, m), 3.65-3.76 (4 H, m), 3.86 (1 H, dd, J = 11.22, 2.52 Hz), 9.74 (1 H, s) | 38 | 344 |

Step 2: Synthesis of Example 10

To a solution of 64 mg (0.19 mmol) of compound F6 in 1,4-dioxane/water (5/1, 6 mL) are added 230 mg (0.38 mmol) of Oxone®. The reaction is stirred at room temperature for 3 h. The reaction mixture is diluted with ethyl acetate (20 mL) and washed with saturated aqueous $NaHCO_3$ solution (2×2 mL). The organic layer is dried ($MgSO_4$), filtered and the filtrate is concentrated under reduced pressure. The residue is purified by column chromatography (silica, eluent: heptanes, 0-20% ethyl acetate) to afford 48 mg of example 10. Yield: 69%; ES-MS: m/z 374 [M+H]; retention time (LC method b): 3.51 min; $^1$H NMR (500 MHz, CHLOROFORM-d) δ ppm 1.45-1.60 (1H, m), 1.68-1.84 (15H, m), 1.88-2.13 (3H, m), 2.24-2.37 (1H, m), 3.01-3.17 (2H, m), 3.37 (1H, dd, J=8.39, 6.71 Hz), 3.70-3.80 (1H, m), 3.81-3.93 (2H, m), 9.25 (1H, s)

Compounds in Table X, amide method D, are made according to this procedure.

LC Method a:
Waters HPLC—ESI+/− ion mode, BEH C18 1.7 mm, 2.1× 50 mm Column; Gradient: 90% A to 5% A in 1.19 minutes hold at 5% A to 1.70 minutes. Flow rate 0.8 mL/min. A=(95% Water 5% Acetonitrile+0.05% Formic Acid) B=(Acetonitrile+0.05% Formic Acid), Diode Array Detector.

Figure 1:
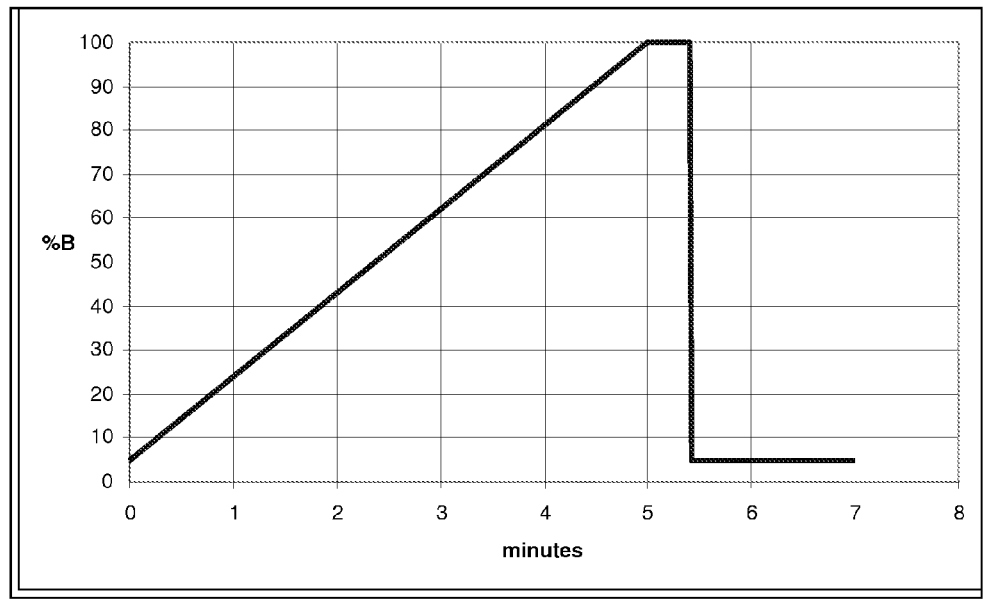
FIG. 1: Described conditions of the LC Method b: HPLC-MS equipment HPLC pumps: Agilent G1312A, Autoinjectors: CTC PAL HTC Detectors: MS: Waters ZQ, UV: Waters 2996 photodiode array, Ancillary: Waters 2420 evaporative light scattering detectors (ELS). Higher specification method designed for medicinal chemistry sample screening.

LC Method b:
HPLC-MS Equipment
HPLC pumps: Agilent G1312A
Autoinjectors: CTC PAL HTC
Detectors: MS: Waters ZQ
  UV: Waters 2996 photodiode array
  Ancillary: Waters 2420 evaporative light scattering detectors (ELS)
  Higher specification method designed for medicinal chemistry sample screening. See FIG. 1

Figure 2:
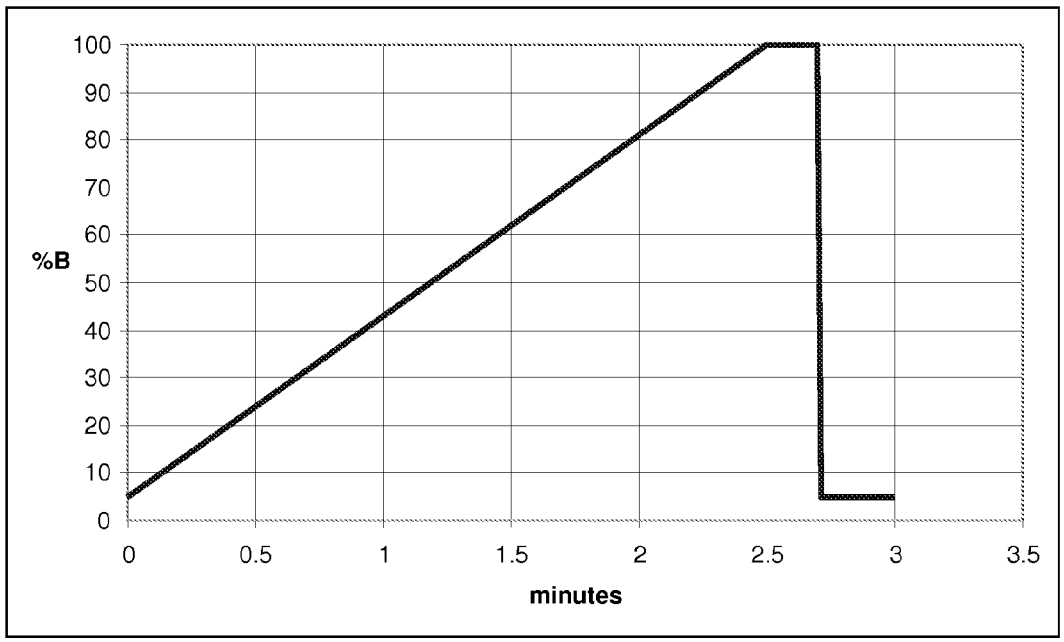
FIG. 2: Described conditions of the LC Method c: HPLC-MS equipment: Shimadzu LCMS-2010EV system: (MS, pump, PDA) Autoinjectors CTC PAL HTS autosampler. Standard method for routine high throughput analysis.

LC Method c:
HPLC-MS Equipment:
Shimadzu LCMS-2010EV system: (MS, pump, PDA)
Autoinjectors CTC PAL HTS autosampler
  Standard method for routine high throughput analysis. See FIG. 2

TABLE X

| Ex | Structure | Acid Method | Amide Method | m/z | retention time | LC-MS method | MW |
|---|---|---|---|---|---|---|---|
| 1 | 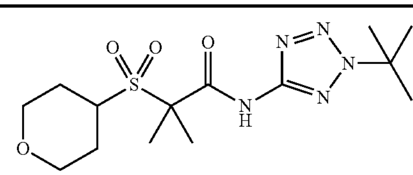 | A | A | 360.1 | 0.70 | a | 359.45 |
| 2 | 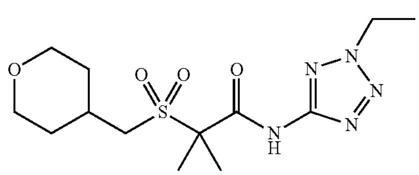 | B | B | 346.2 | 2.91 | b | 345.418 |
| 3 | 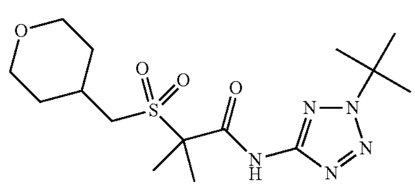 | B | B | 374.1 | 3.47 | b | 373.471 |
| 4 | 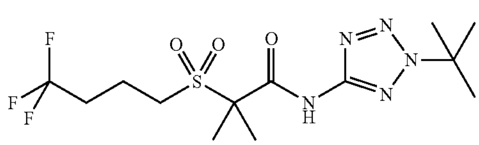 | C | B | 386.0 | 4.02 | b | 385.406 |
| 5 | 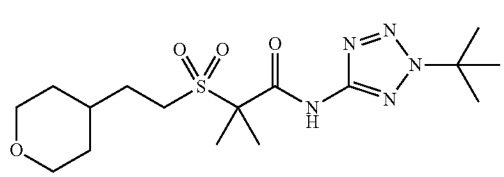 | D | B | 388.2 | 3.67 | b | 387.498 |

TABLE X-continued

| Ex | Structure | Acid Method | Amide Method | m/z | retention time | LC-MS method | MW |
|---|---|---|---|---|---|---|---|
| 6 | 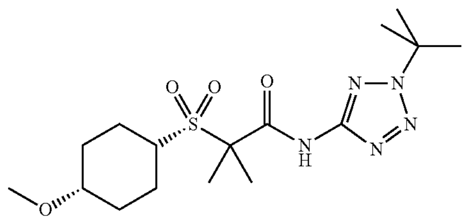 | D | B | 388.3 | 3.79 | b | 387.498 |
| 7 | 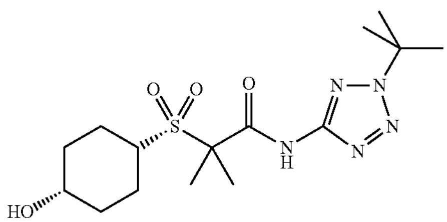 | D | C | 374.3 | 3.30 | b | 373.471 |
| 8 | 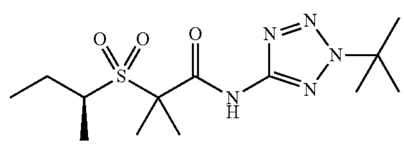 | A | B | 332.3 | 3.96 | b | 331.434 |
| 9 | 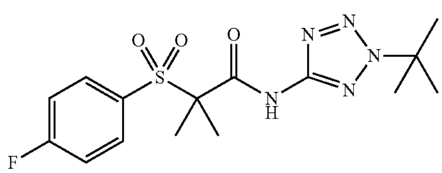 | E | B | 370.1 | 3.73 | b | 369.414 |
| 10 | 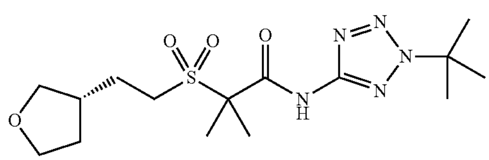 | F | D | 374.3 | 3.51 | b | 373.471 |
| 11 | 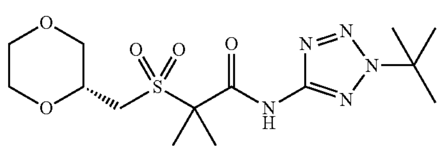 | G | D | 376.2 | 3.37 | b | 375.444 |

Assessment of Biological Properties

The biological properties of the compounds of the formula I are assessed using the assays described below.

A. Human CB1 and CB2 Receptor Binding

Experimental Method:

CB2 membranes are purchased and made from HEK293 EBNA cells stably transfected with human CB2 receptor cDNA (Perkin Elmer Life and Analytical Sciences). CB 1 membranes are isolated from HEK cells stably co-transfected with human CB1 receptor and Gα16 cDNA's. The membrane preparation is bound to scintillation beads (Ysi-Poly-L-lysine SPA beads, GE Healthcare) for 4 h at room temperature in assay buffer containing 50 mM Tris, pH 7.5, 2.5 mM EDTA, 5 mM $MgCl_2$, 0.8% fatty acid free Bovine Serum Albumin. Unbound membrane is removed by washing in assay buffer. Membrane-bead mixture is added to 96-well assay plates in the amounts of 15 ug membrane per well (CB2) or 2.5 ug per well (CB1) and 1 mg SPA bead per well. Compounds are added to the membrane-bead mixture in dose-response concentrations ranging from $1 \times 10^{-5}$M to $1 \times 10^{-10}$ M with 0.25% DMSO, final. The competition reaction is initiated with the addition of $^3$H—CP55940 (Perkin Elmer Life and Analytical Sciences) at a final concentration of 1.5 nM (CB2) or 2.5 nM (CB1). The reaction is incubated at room temperature for 18 h and read on TopCount NXT plate reader. Total and nonspecific binding is determined in the absence and presence of 1.25 uM Win 55212 (Sigma). 1050 values for each compound are calculated as the concentration of compound that inhibits the specific binding of the radioactively labeled ligand to the receptor by 50% using the XLFit 4.1 four parameter logistic model. IC50 values are converted to inhibition constant (Ki) values using Cheng-Prusoff equation.

B. CB2R Mediated Modulation of cAMP Synthesis

Compounds of the invention are evaluated for their CB2 agonist or inverse agonistic activity in accordance with the following experimental method. Compounds which are shown to bind to CB2 by the binding assay described above but which are not shown to exhibit CB2R-mediated modulation of cAMP synthesis by this assay are presumed to be CB2 antagonists.

Experimental Method:

CHO cells expressing human CB2R (Euroscreen) are plated at a density of 5000 cells per well in 384 well plates and incubated overnight at 37° C. After removing the media, the cells are treated with test compounds diluted in stimulation buffer containing 1 mM IBMX, 0.25% BSA and 10 uM Forskolin. The assay is incubated for 30 minutes at 37° C. Cells are lysed and the cAMP concentration is measured using DiscoverX—XS cAMP kit, following the manufacturer's protocol. In this setting, agonists will decrease forskolin induced production of cAMP while inverse agonists will further increase forskolin induced production of cAMP. EC50 of agonists are calculated as follows. The maximal amount of cAMP produced by forskolin compared to the level of cAMP inhibited by 1 uM CP55940 is defined as 100%. The EC50 value of each test compound is determined as the concentration at which 50% of the forskolin-stimulated cAMP synthesis is inhibited. Data is analyzed using a four-parameter logistic model. (Model 205 of XLfit 4.0).

C. CB1R Mediated Modulation of cAMP Synthesis

Compounds of the invention are evaluated for their CB1 agonist or inverse agonistic activity in accordance with the following experimental method. Compounds which are shown to bind to CB1 by the binding assay described above but which are not shown to exhibit CB1R-mediated modulation of cAMP synthesis by this assay are presumed to be CB1 antagonists.

Experimental Method:

CHO cells expressing human CB1R (Euroscreen) are plated at a density of 5000 cells per well in 384 well plates and incubated overnight at 37° C. After removing the media, the cells are treated with test compounds diluted in stimulation buffer containing 1 mM IBMX, 0.25% BSA and 10 uM Forskolin. The assay is incubated for 30 minutes at 37° C. Cells are lysed and the cAMP concentration is measured using DiscoverX—XS cAMP kit, following the manufacturer's protocol. In this setting, agonists will decrease forskolin induced production of cAMP while inverse agonists will further increase forskolin induced production of cAMP. EC50 of agonists are calculated as follows. The maximal amount of cAMP produced by forskolin compared to the level of cAMP inhibited by 1 uM CP55940 is defined as 100%. The EC50 value of each test compound is determined as the concentration at which 50% of the forskolin-stimulated cAMP synthesis is inhibited. Data is analyzed using a four-parameter logistic model. (Model 205 of XLfit 4.0).

Compounds Having Agonist Activity

Through the use of the above described assays compounds are found to exhibit agonistic activity and thus to be particularly well suited for the treatment of pain as well as for the treatment of inflammation. Preferred compounds of the invention will have an activity range of CB2 (<500 nM) and CB1 (>20000).

D. Human Microsomal Stability Assay

The double time point high throughput screen for human liver microsomal metabolic stability is used to measure the in vitro metabolism of test compounds by human liver microsomal enzymes. The data collected are analyzed to calculate a half-life (t½, min) and clearance (expressed as percent hepatic blood flow, % $Q_H$) for test compounds. The assay is performed in 50 mM potassium phosphate buffer, pH 7.4 and 2.5 mM NADPH. Test samples are dissolved in DMSO and acetonitrile for a final assay concentration of 1 uM. Human liver microsomes are diluted in assay buffer to a final assay concentration of 1 mg protein/ml. Compound solution and microsome suspension are added to assay buffer for a final incubation volume of 350 ul. The preparation is incubated for 5 min in a 37° C. water bath. The reaction is started by the addition of NADPH. Volumes of 80 ul are removed from the incubation mix at 0, 5, and 30 min after the start of the reaction and added to 160 ul acetonitrile. The supernatant is transferred to 0.25 mm glass fiber filter plates and centrifuged for 5 min at 3000 rpm. Injection volumes of 10 ul are typically added to HPLC columns with formic acid in water or acetonitrile at a flow rate of 0.3 ml/min. Percent loss of parent compound is calculated from the area under each time point to determine the half-life and clearance. Preferred compounds of the invention will have a human liver microsomal stability of <25% $Q_H$.

E. Aqueous Solubility Assay

The equilibrium solubility of compounds is determined in pH 2, 4.5, 6.8 buffers. Prior to solubility measurement, the crystalline/amorphous characteristics of the sample are determined by observing the powder form under polarized light microscope. Solubility is only measured when compound is crystalline.

Approximately 2 mg of compound are weighed out into a vial and 1-2 ml of buffer are added into the vial (pHs 2 & 4.5, use 1 ml and for pHs 6.8 and 7.4 use 2 ml of buffer). The vial is rotated for 48 hrs protected from light. After 48 hrs, the sample is transferred into an eppendorf tube and centrifuged for 10 minutes at 14,000 RPM, if the supernatant is not clear, it is filtered (PVDF filter). The clear supernatant is diluted if necessary, before analyzing via HPLC. The final pH of the supernatant or the filtrate is measured and reported. The external calibration curve is used to determine the solubility value. The percentage of extraneous peaks relative to the parent peak is monitored in the standard solution as well as the solubility sample. Preferred compounds of the invention will have a solubility of >100 µg/ml.

F. Ames Mutagenicity Assay: Bacteria Reverse Mutation Screening Assay

The Ames [1] *Salmonella* bacterial strains used in the abbreviated screening assay [2] are TA98 and TA100. Actively growing (log phase) bacteria are incubated with test compound and trace amounts of histidine in the presence or absence of S9 for 48 hours on minimal agar plates. Test compound is dissolved in DMSO to a final concentration of 100 mg/ml. The stock is serially diluted to yield concentrations of 100, 50, 25 12.5 and 6.3 mg/ml. Fifty microliters of dosing solution is combined with top agar and buffer (or S9 mix) and poured on duplicate plates to yield effective doses of 5000, 2500, 1250, 625 and 313 µg/plate. Positive and negative controls plates are included. Formation of colonies after 48 hr incubation at 37° C. is an indication of genetic reversion, either arising spontaneously or caused by the test compound. The average number of spontaneous colonies growing on control plates is compared to the number of colonies on test plates. A fold increase of 2-3× over background is generally considered a positive response for mutagenicity.

1. Maron, D. M. and Ames, B. N. (1983). "Revised Methods for the Salmonella Mutagenicity Test". *Mutat. Res.* 113, 173-215.
2. D. A. Burke, D. J. Wedd, and B. Burlinson (1996). "Use of the Miniscreen assay to screen novel compounds for bacterial mutagenicity in the pharmaceutical industry". Mutagenesis 11: 201-205.

The compounds of this invention demonstrate a low activation of the CB1 receptor. Since it is believed that the highly selective activation of the CB2 receptor with an agonist may offer avenues of harnessing the beneficial effects while avoiding the adverse effects seen with dual CB1/CB2 cannabinoid receptor agonists (see e.g. Expert Opinion on Investigational Drugs (2005), 14(6), 695-703) it is desirable to provide agonists of CB2 with minimized CB1 activity. Slow metabolism of compounds is desirable to ensure prolonged exposure of the compound. This can be demonstrated by a low clearance in vitro in human liver microsomes (preferred<25% $Q_H$). Further, it is required that the compounds have good solubility (preferred >100 μg/ml) to ensure oral bioavailability and linear PK. The compounds of the invention possess all four desirable properties described hereinabove for CB2, CB1, HLM stability and Ames, as shown in Table XI.

TABLE XI

| Example | MOLSTRUCTURE | CB2 CAMP EC50 [nM] | CB1 CAMP EC50 [nM] | HLM [QH %] | solubility at pH 6.8; pH 4.5 [μg/ml] | Ames |
| --- | --- | --- | --- | --- | --- | --- |
| Table II compound 1 | | 21 | >50000 | <30.10 | >1753; >2121 | negative |
| Example 67 WO08039645 | | 12 | 11400 | 79 | 16; 15 | negative |
| Example 69 WO08039645 | | 216 | >20000 | <30.10 | 1232; 1043 | positive |
| Example 66 WO08039645 | | 0.72 | >50000 | 57 | 53; 56 | negative |
| Table II compound 2 | | 50 | >50000 | <30.10 | 353; 391 | negative |
| Example 56 WO08039645 | | 4.5 | >20000 | 47 | 44; 47 | negative |
| Example 57 WO08039645 | | 23 | 2400 | 87 | 406; 383 | negative |

TABLE XI-continued

| Example | MOLSTRUCTURE | CB2 CAMP EC50 [nM] | CB1 CAMP EC50 [nM] | HLM [QH %] | solubility at pH 6.8; pH 4.5 [μg/ml] | Ames |
|---|---|---|---|---|---|---|
| Example 59 WO08039645 | | 140 | >20000 | <30.10 | 452; 396 | positive |
| Table II compound 6 | | 22 | 39500 | <30 | 122; 133 | negative |
| Example 248 WO08014199 | | 0.98 | 3290 | 32 | 1.25; 1.68 | negative |
| Example 251 WO08014199 | | 2.57 | 10900 | 30 | 148; 137 | positive |
| Example 252 WO08014199 | | 0.401 | 934 | 85 | 1.62; 1.74 | negative |
| Example 130 WO08014199 | | 2.4 | 2240 | 68 | 4.7; 5.2 | negative |

TABLE XI-continued

| Example | MOLSTRUCTURE | CB2 CAMP EC50 [nM] | CB1 CAMP EC50 [nM] | HLM [QH %] | solubility at pH 6.8; pH 4.5 [µg/ml] | Ames |
|---|---|---|---|---|---|---|
| Table II compound 5 | | 101 | >50000 | <30.10 | 1150, 1208 | negative |
| Example 42 WO08039645 | | 19 | >20000 | 68 | 19 8; 20 | negative |
| Example 43 WO08039645 | | 642 | >20000 | 61 | 1158; 1263 | positive |
| Example 44 WO08039645 | | 14 | 10700 | 67 | 11 8; 13 | negative |

Therapeutic Use

As can be demonstrated by the assays described above, the compounds of the invention are useful in modulating the CB2 receptor function. By virtue of this fact, these compounds have therapeutic use in treating disease-states and conditions mediated by the CB2 receptor function or that would benefit from modulation of the CB2 receptor function.

As the compounds of the invention modulate the CB2 receptor function, they have very useful anti-inflammatory and immune-suppressive activity and they can be used in patients as drugs, particularly in the form of pharmaceutical compositions as set forth below, for the treatment of disease-states and conditions.

As noted before, those compounds which are CB2 agonists can also be employed for the treatment of pain.

The agonist, antagonist and inverse agonist compounds according to the invention can be used in patients as drugs for the treatment of the following disease-states or indications that are accompanied by inflammatory processes:

(i) Lung diseases: e.g. asthma, bronchitis, allergic rhinitis, emphysema, adult respiratory distress syndrome (ARDS), pigeon fancier's disease, farmer's lung, chronic obstructive pulmonary disease (COPD), asthma including allergic asthma (atopic or non-atopic) as well as exercise-induced bronchoconstriction, occupational asthma, viral- or bacterial exacerbation of asthma, other non-allergic asthmas and "wheezy-infant syndrome", pneumoconiosis, including aluminosis, anthracosis, asbestosis, chalicosis, ptilosis, siderosis, silicosis, tabacosis and byssinosis;

(ii) Rheumatic diseases or autoimmune diseases or musculoskeletal diseases: all forms of rheumatic diseases, especially rheumatoid arthritis, acute rheumatic fever, and polymyalgia rheumatica; reactive arthritis; rheumatic soft tissue diseases; inflammatory soft tissue diseases of other genesis; arthritic symptoms in degenerative joint diseases (arthroses); tendinitis, bursitis, osteoarthritis, traumatic arthritis; collagenoses of any genesis, e.g., systemic lupus erythematosus, scleroderma, polymyositis, dermatomyositis, Sjögren syndrome, Still disease, Felty syndrome; and osteoporosis and other bone resorption diseases;

(iii) Allergic diseases: all forms of allergic reactions, e.g., angioneurotic edema, hay fever, insect bites, allergic reactions to drugs, blood derivatives, contrast agents, etc., anaphylactic shock (anaphylaxis), urticaria, angioneurotic edema, and contact dermatitis;

(iv) Vascular diseases: panarteritis nodosa, polyarteritis nodosa, periarteritis nodosa, arteritis temporalis, Wegner granulomatosis, giant cell arthritis, atherosclerosis, reperfusion injury and erythema nodosum;

(v) Dermatological diseases: e.g. dermatitis, psoriasis; sunburn, burns, eczema;

(vi) Renal diseases: e.g. nephrotic syndrome; and all types of nephritis, e.g., glomerulonephritis; pancreatits;
(vii) Hepatic diseases: e.g. acute liver cell disintegration; acute hepatitis of various genesis, e.g., viral, toxic, drug-induced; and chronically aggressive and/or chronically intermittent hepatitis;
(viii) Gastrointestinal diseases: e.g. inflammatory bowel diseases, irritable bowel syndrome, regional enteritis (Crohns disease), colitis ulcerosa; gastritis; aphthous ulcer, celiac disease, regional ileitis, gastroesophageal reflux disease;
(ix) Neuroprotection: e.g. in the treatment of neurodegeneration following stroke; cardiac arrest; pulmonary bypass; traumatic brain injury; spinal cord injury or the like;
(x) Eye diseases: allergic keratitis, uveitis, or iritis; conjunctivitis; blepharitis; neuritis nervi optici; choroiditis; glaucoma and sympathetic ophthalmia;
(xi) Diseases of the ear, nose, and throat (ENT) area: e.g. tinnitus; allergic rhinitis or hay fever; otitis externa; caused by contact eczema, infection, etc.; and otitis media;
(xii) Neurological diseases: e.g. brain edema, particularly tumor-related brain edema; multiple sclerosis; acute encephalomyelitis; meningitis; acute spinal cord injury; trauma; dementia, particularly degenerative dementia (including senile dementia, Alzheimer's disease; Parkinson's disease and Creutzfeldt-Jacob disease; Huntington's chorea, Pick's disease; motor neuron disease), vascular dementia (including multi-infarct dementia) as well as dementia associated with intracranial space occupying lesions; infections and related conditions (including HIV infection); Guillain-Barre syndrome; myasthenia gravis, stroke; and various forms of seizures, e.g., nodding spasms;
(xiii) Blood diseases: acquired hemolytic anemia; aplastic anemia, and idiopathic thrombocytopenia;
(xiv) Tumor diseases: acute lymphatic leukemia; Hodgkin's disease, malignant lymphoma; lymphogranulomatoses; lymphosarcoma; solid malignant tumors; extensive metastases;
(xv) Endocrine diseases: endocrine ophthalmopathy; endocrine orbitopathia; thyrotoxic crisis; Thyroiditis de Quervain; Hashimoto thyroiditis; Morbus Basedow; granulomatous thyroiditis; struma lymphomatosa; and Graves disease; type I diabetes (insulin-dependent diabetes);
(xvi) Organ and tissue transplantations and graft-versus-host diseases;
(xvii) Severe states of shock, e.g., septic shock, anaphylactic shock, and systemic inflammatory response syndrome (SIRS);
(xviii) Acute pain such as dental pain, perioperative, postoperative pain, traumatic pain, muscle pain, pain in burned skin, sun burn, trigeminal neuralgia, sun burn; spasm of the gastrointestinal tract or uterus, colics;
(xix) Visceral pain such as pain associated with chronic pelvic pain, pancreatitis, peptic ulcer, interstitial cystitis, renal colic, angina, dysmenorrhoea, menstruation, gynaecological pain, irritable bowel syndrome (IBS), non-ulcer dyspepsia, non-cardiac chest pain, myocardial ischemia;
(xx) Neuropathic pain such as low back pain, non-herpetic neuralgia, post herpetic neuralgia, diabetic neuropathy, nerve injury, acquired immune deficiency syndrome (AIDS) related neuropathic pain, head trauma, painful traumatic mononeuropathy, toxin and chemotherapy induced pain, phantom limb pain, painful polyneuropathy, thalamic pain syndrome, post-stroke pain, central nervous system injury, post surgical pain, stump pain, repetitive motion pain, pain induced by post mastectomy syndrome, multiple sclerosis, root avulsions, postthoracotomy syndrome, neuropathic pain associated hyperalgesia and allodynia.
(xxi) Inflammatory/nociceptive pain induced by or associated with disorders such as osteoarthritis, rheumatoid arthritis, rheumatic disease, teno-synovitis, gout, vulvodynia, myofascial pain (muscular injury, fibromyalgia), tendonitis, osteoarthritis, juvenile arthritis, spondylitis, gouty arthritis, psoriatic arthritis, muscoskeletal pain, fibromyalgia, sprains and strains, sympathetically maintained pain, myositis, pain associated with migraine, toothache, influenza and other viral infections such as the common cold, rheumatic fever, systemic lupus erythematosus;
(xxii) Cancer pain induced by or associated with tumors such as lymphatic leukemia; Hodgkin's disease, malignant lymphoma; lymphogranulomatoses; lympho sarcoma; solid malignant tumors; extensive metastases;
(xxiii) Headache such as cluster headache, migraine with and without aura, tension type headache, headache with different origins, headache disorders including prophylactic and acute use;
(xxiv) various other disease-states or conditions including, restenosis following percutaneous transluminal coronary angioplasty, acute and chronic pain, atherosclerosis, reperfusion injury, congestive heart failure, myocardial infarction, thermal injury, multiple organ injury secondary to trauma, necrotizing enterocolitis and syndromes associated with hemodialysis, leukopheresis, and granulocyte transfusion, sarcoidosis, gingivitis, pyrexia. edema resulting from trauma associated with burns, sprains or fracture, cerebral oedema and angioedema, Diabetes such as diabetic vasculopathy, diabetic neuropathy, diabetic retinopathy, post capillary resistance or diabetic symptoms associated with insulitis (e.g. hypergiycemia, diuresis, proteinuria and increased nitrite and kallikrein urinary excretion).

Other indications include: epilepsy, septic shock e.g. as antihypovolemic and/or antihypotensive agents, cancer, sepsis, osteoporosis, benign prostatic hyperplasia and hyperactive bladder, pruritis, vitiligo, general gastrointestinal disorders, disturbances of visceral motility at respiratory, genitourinary, gastrointestinal or vascular regions, wounds, burns, tissue damage and postoperative fever, syndromes associated with Itching.

Besides being useful for human treatment, these compounds are also useful for veterinary treatment of companion animals, exotic animals and farm animals, including mammals, rodents, and the like.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For Example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased inhibitory activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for Example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by Remington: The Science and Practice of Pharmacy, 20th Edition, A. Gennaro (ed.), Lippincott Williams & Wilkins, 2000; Handbook of Pharmaceutical Additives, Michael & Irene Ash (eds.), Gower, 1995; Handbook of Pharmaceutical Excipients, A. H. Kibbe (ed.), American Pharmaceutical Ass'n, 2000; H. C. Ansel and N. G. Popovish, Pharmaceutical Dosage Forms and Drug Delivery Systems, 5th ed., Lea and Febiger, 1990; each of which is incorporated herein by reference in their entireties to better describe the state of the art.

As one of skill in the art would expect, the forms of the compounds of the invention utilized in a particular pharmaceutical formulation will be selected (e.g., salts) that possess suitable physical characteristics (e.g., water solubility) that is required for the formulation to be efficacious.

Pharmaceutical compositions suitable for buccal (sub-lingual) administration include lozenges comprising a compound of the present invention in a flavored base, usually sucrose, and acacia or tragacanth, and pastilles comprising the compound in an inert base such as gelatin and glycerin or sucrose and acacia.

Pharmaceutical compositions suitable for parenteral administration comprise sterile aqueous preparations of a compound of the present invention. These preparations are preferably administered intravenously, although administration can also be effected by means of subcutaneous, intramuscular, or intradermal injection. Injectable pharmaceutical formulations are commonly based upon injectable sterile saline, phosphate-buffered saline, oleaginous suspensions, or other injectable carriers known in the art and are generally rendered sterile and isotonic with the blood. The injectable pharmaceutical formulations may therefore be provided as a sterile injectable solution or suspension in a nontoxic parenterally acceptable diluent or solvent, including 1,3-butanediol, water, Ringer's solution, isotonic sodium chloride solution, fixed oils such as synthetic mono- or diglycerides, fatty acids such as oleic acid, and the like. Such injectable pharmaceutical formulations are formulated according to the known art using suitable dispersing or setting agents and suspending agents. Injectable compositions will generally contain from 0.1 to 5% w/w of a compound of the invention.

Solid dosage forms for oral administration of the compounds include capsules, tablets, pills, powders, and granules. For such oral administration, a pharmaceutically acceptable composition containing a compound(s) of the invention is formed by the incorporation of any of the normally employed excipients, such as, for example, pharmaceutical grades of mannitol, lactose, starch, pregelatinized starch, magnesium stearate, sodium saccharine, talcum, cellulose ether derivatives, glucose, gelatin, sucrose, citrate, propyl gallate, and the like. Such solid pharmaceutical formulations may include formulations, as are well-known in the art, to provide prolonged or sustained delivery of the drug to the gastrointestinal tract by any number of mechanisms, which include, but are not limited to, pH sensitive release from the dosage form based on the changing pH of the small intestine, slow erosion of a tablet or capsule, retention in the stomach based on the physical properties of the formulation, bioadhesion of the dosage form to the mucosal lining of the intestinal tract, or enzymatic release of the active drug from the dosage form.

Liquid dosage forms for oral administration of the compounds include emulsions, microemulsions, solutions, suspensions, syrups, and elixirs, optionally containing pharmaceutical adjuvants in a carrier, such as, for example, water, saline, aqueous dextrose, glycerol, ethanol and the like. These compositions can also contain additional adjuvants such as wetting, emulsifying, suspending, sweetening, flavoring, and perfuming agents.

Topical dosage forms of the compounds include ointments, pastes, creams, lotions, gels, powders, solutions, sprays, inhalants, eye ointments, eye or ear drops, impregnated dressings and aerosols, and may contain appropriate conventional additives such as preservatives, solvents to assist drug penetration and emollients in ointments and creams. Topical application may be once or more than once per day depending upon the usual medical considerations. Furthermore, preferred compounds for the present invention can be administered in intranasal form via topical use of suitable intranasal vehicles. The formulations may also contain compatible conventional carriers, such as cream or ointment bases and ethanol or oleyl alcohol for lotions. Such carriers may be present as from about 1% up to about 98% of the formulation, more usually they will form up to about 80% of the formulation.

Transdermal administration is also possible. Pharmaceutical compositions suitable for transdermal administration can be presented as discrete patches adapted to remain in intimate contact with the epidermis of the recipient for a prolonged period of time. To be administered in the form of a transdermal delivery system, the dosage administration will, of course, be continuous rather than intermittent throughout the dosage regimen. Such patches suitably contain a compound of the invention in an optionally buffered, aqueous solution, dissolved and/or dispersed in an adhesive, or dispersed in a polymer. A suitable concentration of the active compound is about 1% to 35%, preferably about 3% to 15%.

For administration by inhalation, the compounds of the invention are conveniently delivered in the form of an aerosol spray from a pump spray device not requiring a propellant gas or from a pressurized pack or a nebulizer with the use of a suitable propellant, e.g., dichlorodifluoromethane, trichlorofluoromethane, dichlorotetrafluoroethane, tetrafluoroethane, heptafluoropropane, carbon dioxide, or other suitable gas. In any case, the aerosol spray dosage unit may be determined by providing a valve to deliver a metered amount so that the resulting metered dose inhaler (MDI) is used to administer the compounds of the invention in a reproducible and controlled way. Such inhaler, nebulizer, or atomizer devices are known in the prior art, for example, in PCT International Publication Nos. WO 97/12687 (particularly FIG. 6 thereof, which is the basis for the commercial RESPIMAT® nebulizer); WO 94/07607; WO 97/12683; and WO 97/20590, to which reference is hereby made and each of which is incorporated herein by reference in their entireties.

Rectal administration can be effected utilizing unit dose suppositories in which the compound is admixed with low-melting water-soluble or insoluble solids such as fats, cocoa butter, glycerinated gelatin, hydrogenated vegetable oils, mixtures of polyethylene glycols of various molecular weights, or fatty acid esters of polyethylene glycols, or the like. The active compound is usually a minor component, often from about 0.05 to 10% by weight, with the remainder being the base component.

In all of the above pharmaceutical compositions, the compounds of the invention are formulated with an acceptable carrier or excipient. The carriers or excipients used must, of course, be acceptable in the sense of being compatible with the other ingredients of the composition and must not be deleterious to the patient. The carrier or excipient can be a solid or a liquid, or both, and is preferably formulated with the compound of the invention as a unit-dose composition, for example, a tablet, which can contain from 0.05% to 95% by weight of the active compound. Such carriers or excipients include inert fillers or diluents, binders, lubricants, disintegrating agents, solution retardants, resorption accelerators, absorption agents, and coloring agents. Suitable binders include starch, gelatin, natural sugars such as glucose or β-lactose, corn sweeteners, natural and synthetic gums such as acacia, tragacanth or sodium alginate, carboxymethylcellulose, polyethylene glycol, waxes, and the like. Lubricants include sodium oleate, sodium stearate, magnesium stearate, sodium benzoate, sodium acetate, sodium chloride, and the like. Disintegrators include starch, methyl cellulose, agar, bentonite, xanthan gum, and the like.

Pharmaceutically acceptable carriers and excipients encompass all the foregoing additives and the like.

The invention claimed is:

1. A compound of the formula (I)

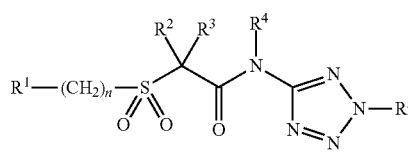

(I)

wherein:
$R^1$ is $C_{1-10}$ alkyl, $C_{1-10}$ alkoxy, $C_{3-10}$ cycloalkyl, 3-10 membered saturated heterocyclic ring or aryl each optionally independently substituted with 1-3 substituents chosen from $C_{1-4}$ alkyl, $C_{1-4}$ alkoxy, $C_{3-10}$ cycloalkyl, $C_{1-4}$ alkylsulfonyl, acyl, oxo, cyano, phenyl, hydroxyl and halogen;

$R^2$ and $R^3$ are $C_{1-4}$ alkyl or hydrogen with the proviso that both $R^2$ and $R^3$ cannot be hydrogen; or $R^2$ and $R^3$ together with the carbon atom to which they are attached form a 3- to 6-membered cycloalkyl or heterocyclic ring;

$R^4$ is hydrogen or methyl;

$R^5$ is chosen from $C_{1-10}$ alkyl, $C_{1-10}$ alkoxy, $C_{3-10}$ cycloalkyl, 3-10 membered saturated heterocyclic ring, 5-6 membered heteroaryl ring and aryl each optionally independently substituted with 1-3 substituents chosen from $C_{1-4}$ alkyl, $C_{1-4}$ alkoxy, $C_{3-10}$ cycloalkyl, $C_{1-4}$ alkylsulfonyl, acyl, oxo, cyano, hydroxyl and halogen;

n is 0, 1 or 2;

wherein any carbon atom on the formula (I) or any R substituent listed above is optionally partially or fully halogenated where possible;

or a pharmaceutically acceptable salt thereof.

2. The compound according to claim 1, and wherein
$R^1$ is $C_{1-5}$ alkyl, phenyl, cyclopropyl, cyclobutyl, cyclopentyl, cyclohexyl, cycloheptyl, cyclooctyl, tetrahydrofuranyl, tetrahydropyranyl, azetidinyl, piperidinyl; dioxanyl, thiomorpholinyl, 1,1-Dioxo-1λ%$^6$-thiomorpholinyl, morpholinyl, pyrrolidinyl, piperazinyl, and Dihydro-2H-quinolinyl, each optionally substituted by 1-3 substituents chosen from halogen, $C_{1-4}$ alkyl, $C_{1-4}$ alkoxy and hydroxyl;

$R^2$ and $R^3$ are independently methyl, ethyl, n-propyl, isopropyl, or hydrogen with the proviso that both $R^2$ and $R^3$ cannot be hydrogen; or $R^2$ and $R^3$ together with the carbon to which they are attached form a cyclopropyl, cyclobutyl, or cyclopentyl ring;

$R^4$ is hydrogen;

$R^5$ is $C_{1-5}$ alkyl.

3. The compound according to claim 2, and wherein $R^2$ and $R^3$ are methyl.

4. The compound according to claim 3, and wherein $R^1$ is $C_{1-4}$ alkyl, phenyl, cyclohexyl, tetrahydrofuranyl, tetrahydropyranyl or dioxanyl, each optionally substituted by 1-3 substituents chosen from halogen, $C_{1-4}$ alkyl, $C_{1-4}$ alkoxy and hydroxyl;

$R^5$ is methyl, ethyl, propyl, butyl or t-butyl.

5. The compound according to claim 4, and wherein $R^5$ is t-butyl.

6. The compound according to claim 5, and wherein the combination $R^1(CH_2)_n$— is

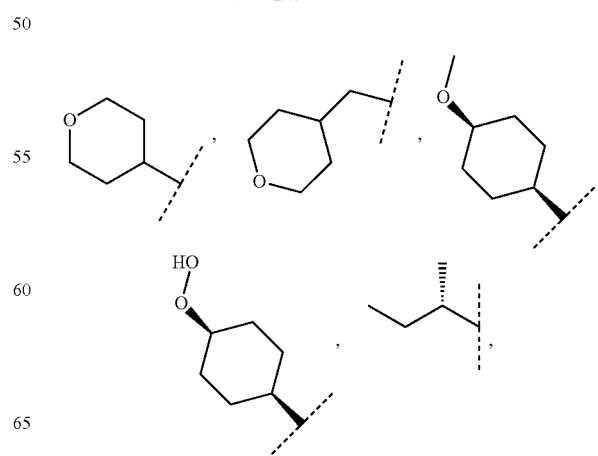

-continued
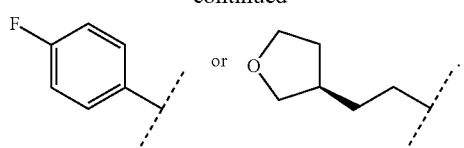
7. A compound chosen from
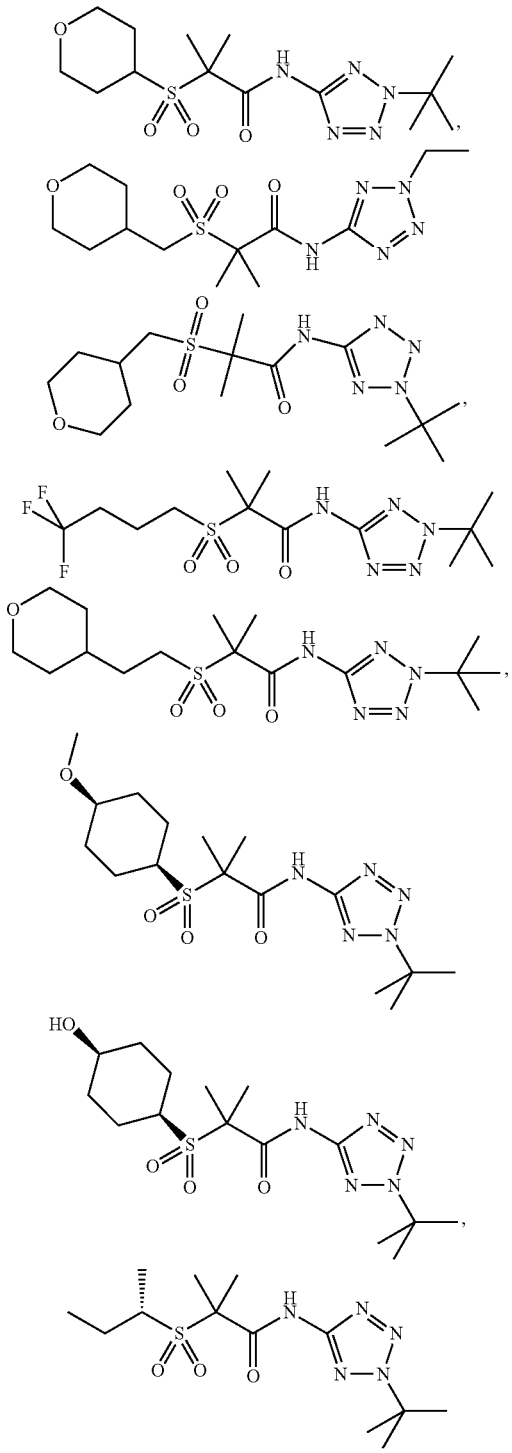
-continued
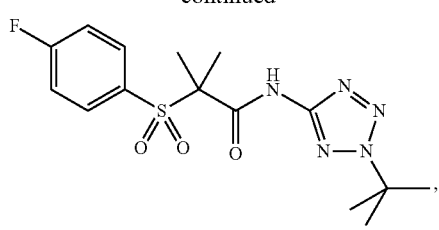
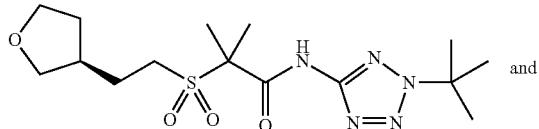
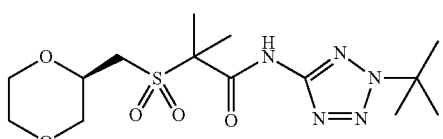
or a pharmaceutically acceptable salt thereof.
8. A compound chosen from:
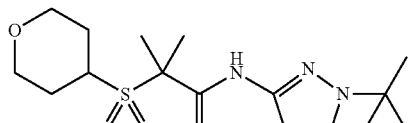
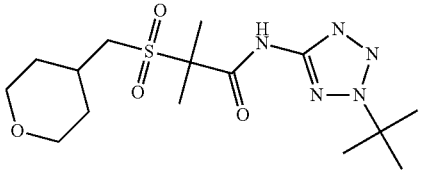
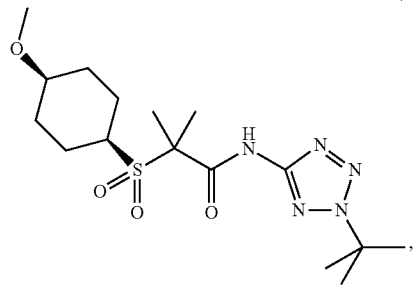

-continued

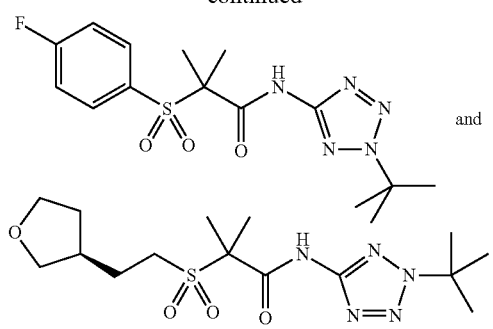 and or a pharmaceutically acceptable salt thereof.

9. A pharmaceutical composition comprising a therapeutically effective amount of a compound according to claim 1 and one or more pharmaceutically acceptable carriers and/or adjuvants.

10. A method of treating pain comprising administering a therapeutically effective amount of a compound according to claim 1.

11. The method according to claim 10 wherein pain is chosen from acute pain, visceral pain, neuropathic pain, inflammatory and nociceptive pain, cancer pain and headache.

* * * * *